US012343154B2

(12) United States Patent
Wu et al.

(10) Patent No.: US 12,343,154 B2
(45) Date of Patent: Jul. 1, 2025

(54) ELECTROCARDIOGRAM WAVEFORM RECONSTRUCTION FROM PHOTOPLETHYSMOGRAM

(71) Applicant: UNIVERSITY OF MARYLAND, COLLEGE PARK, College Park, MD (US)

(72) Inventors: Min Wu, Clarksville, MD (US); Qiang Zhu, College Park, MD (US); Xin Tian, College Park, MD (US); Chau-Wai Wong, Apex, NC (US)

(73) Assignee: UNIVERSITY OF MARYLAND, COLLEGE PARK, College Park, MD (US)

( * ) Notice: Subject to any disclaimer, the term of this patent is extended or adjusted under 35 U.S.C. 154(b) by 484 days.

(21) Appl. No.: 17/598,083

(22) PCT Filed: Mar. 26, 2020

(86) PCT No.: PCT/US2020/025051
§ 371 (c)(1),
(2) Date: Sep. 24, 2021

(87) PCT Pub. No.: WO2020/198522
PCT Pub. Date: Oct. 1, 2020

(65) Prior Publication Data
US 2022/0183606 A1 Jun. 16, 2022

Related U.S. Application Data

(60) Provisional application No. 62/824,134, filed on Mar. 26, 2019.

(51) Int. Cl.
A61B 5/352 (2021.01)
A61B 5/029 (2006.01)
G16H 50/30 (2018.01)

(52) U.S. Cl.
CPC ............. *A61B 5/352* (2021.01); *A61B 5/029* (2013.01); *G16H 50/30* (2018.01)

(58) Field of Classification Search
None
See application file for complete search history.

(56) References Cited

U.S. PATENT DOCUMENTS

2016/0007864 A1* 1/2016 Scharf ................. A61B 5/7278
600/301
2016/0081563 A1* 3/2016 Wiard ................. A61B 5/7278
600/485

(Continued)

FOREIGN PATENT DOCUMENTS

CN 104706349 A 6/2015

OTHER PUBLICATIONS

Q. Zhu et al., "ECG Reconstruction via Ppg: A Pilot Study", Department of Electrical and Computer Engineering, University of Maryland, College Park, USA, Department of Electrical and Computer Engineering, North Carolina State University, Raleigh, USA, 4 pages.

(Continued)

Primary Examiner — Ankit D Tejani
(74) Attorney, Agent, or Firm — SQUIRE PATTON BOGGS (US) LLP

(57) ABSTRACT

Systems, methods, apparatuses, and computer program for reconstructing electrocardiogram (ECG) waveforms from photoplethysmogram (PPG). A method for cardiovascular monitoring and analytics may include obtaining an electrical signal of a heart. The method may also include obtaining a circulatory signal related to a pulsatile volume of blood in tissue. The method may also include preprocessing the electrical signal and the circulatory signal. The method may further include training a mapping using the preprocessed electrical signal and circulatory signal. In addition, the (Continued)

method may include deriving cardiovascular data based on the trained mapping of the preprocessed electrical signal or circulatory signal.

18 Claims, 17 Drawing Sheets

(56) References Cited

U.S. PATENT DOCUMENTS

2017/0112415 A1* 4/2017 Choi ................... G06V 40/20
2019/0117096 A1* 4/2019 Rundo ............... A61B 5/02405

OTHER PUBLICATIONS

R. Banerjee, et al., "Estimation of ECG Parameters using Photoplethysmography", Downloaded on May 17, 2020 UTC from IEEE Xplore, 5 pages.

Q. Zhu, Electrocardiogram (ECG) Reconstruction From Photoplethysmogram (PPG), research blog post, published in Electrical and Computer Engineering, University and Maryland, College Park, 2018, https://zhuqiangumd.github.io/eaearch/2018-ECG_recon_from_PPG, 2 pages.

International Search Report and Written Opinion issued in corresponding PCT Application No. PCT/US2020/025051 on Jun. 4, 2020.

Andrew Reisner et al., "Utility of the Photoplethysmogram in Circulatory Monitoring", Review Article, Anesthesiology 2008; 108:950-8, 9 pages.

Mika P. Tarvainen et al., "An Advanced Detrending Method with Application to HRV Analysis", IEEE Transactions on Biomedical Engineering, vol. 49, No. 2, Feb. 2002, Publisher Item Identifier: S 0018-9294(02)00637-7, 4 pages.

John Allen, "Photoplethysmography and its application in clinical physiological measurement", Physiological Measurement 28 (2007) R1-R39, DOI: 10.1088/0967-3334/28/3/R01, 40 pages.

Qiang Zhu et al., "Learning Your Heart Actions From Pulse: ECG Waveform Reconstruction From PPG", IEEE Internet of Things Journal, vol. 8, No. 23, Dec. 1, 2021, DOI: 10.1109/JIOT.2021.3097946, 15 pages.

* cited by examiner

Confusion matrix from number of PCs = 100

| True Class \ Predicted Class | CHF | STMI | NSTMI | HYPO | CAD |
|---|---|---|---|---|---|
| CHF | 100.0% | 0.0% | 0.0% | 0.0% | 0.0% |
| STMI | 0.0% | 100.0% | 0.0% | 0.0% | 0.0% |
| NSTMI | 0.0% | 0.0% | 100.0% | 0.0% | 0.0% |
| HYPO | 0.0% | 1.8% | 0.0% | 98.2% | 0.0% |
| CAD | 0.0% | 0.0% | 0.0% | 0.0% | 100.0% |

FIG. 12A

Confusion matrix from number of PCs = 100

| True Class \ Predicted Class | CHF | STMI | NSTMI | HYPO | CAD |
|---|---|---|---|---|---|
| CHF | 100.0% | 0.0% | 0.0% | 0.0% | 0.0% |
| STMI | 0.0% | 100.0% | 0.0% | 0.0% | 0.0% |
| NSTMI | 4.3% | 0.0% | 95.7% | 0.0% | 0.0% |
| HYPO | 0.0% | 0.0% | 0.0% | 100.0% | 0.0% |
| CAD | 0.0% | 0.0% | 0.0% | 0.0% | 100.0% |

FIG. 12B

Confusion matrix from number of PCs = 100

| True Class \ Predicted Class | CHF | STMI | NSTMI | HYPO | CAD |
|---|---|---|---|---|---|
| CHF | 81.5% | 4.6% | 9.2% | 1.5% | 3.1% |
| STMI | 8.5% | 83.1% | 5.1% | 3.4% | 0.0% |
| NSTMI | 22.5% | 17.5% | 55.0% | 2.5% | 2.5% |
| HYPO | 1.8% | 3.5% | 1.8% | 93.0% | 0.0% |
| CAD | 6.5% | 22.6% | 19.4% | 0.0% | 51.6% |

FIG. 12C

ELECTROCARDIOGRAM WAVEFORM RECONSTRUCTION FROM PHOTOPLETHYSMOGRAM

CROSS-REFERENCE TO RELATED APPLICATIONS

This application claims priority from U.S. provisional patent application Ser. No. 62/824,134 filed on Mar. 26, 2019. The contents of this earlier filed application are hereby incorporated by reference in their entirety.

FIELD

Some embodiments may generally relate to heart actions from pulse. For example, certain example embodiments may relate to apparatuses, systems, and/or methods for reconstructing electrocardiogram (ECG) waveforms from photoplethysmogram (PPG). Other embodiments may use intermediate results of such reconstruction or post-processed result to perform inference on the heart action or health condition.

BACKGROUND

Cardiovascular disease (CVD) has become the leading cause of human death—about 32% of all deaths worldwide in 2017 according to the Global Burden of Disease results. Statistics also reveal that young people, especially athletes, are more prone to sudden cardiac arrests than before. Those life-threatening cardiovascular diseases often happen outside clinics and hospitals, and the patients are recommended by cardiologists to attend a long-term continuous monitoring program.

The electrocardiogram (ECG) is a fundamental tool of clinical practice, and the most commonly used cardiovascular diagnostic procedure today. Many modern wearable ECG systems have been developed in recent decades. They have a simpler physical configuration, they are more reliable than before, and many weigh only a fraction of a pound. However, the ECG stickers are prone to cause skin irritation and discomfort during prolonged use, which restricts the long-term use of the devices. In addition, there are long-term monitoring concerns due to the reliance on the active involvement of users.

The photoplethysmogram (PPG) is another means of obtaining cardiovascular data. PPG is a noninvasive circulatory signal related to the pulsatile volume of blood in tissue. The PPG and ECG signals are intrinsically related. As there is a prevailing use of wearable devices capturing users' daily PPG signal, there is a need to utilize this cardiovascular relation to reconstruct the ECG waveform from the PPG measurement.

SUMMARY

Some embodiments are directed to a method for cardiovascular monitoring and analytics. The method may include obtaining an electrical signal of a heart. The method may also include obtaining a circulatory signal related to a pulsatile volume of blood in tissue. The method may further include preprocessing the electrical signal and the circulatory signal. In addition, the method may include training a mapping using the preprocessed electrical signal and circulatory signal. Further, the method may include deriving cardiovascular data based on the trained mapping of the preprocessed electrical signal or circulatory signal.

Other embodiments is directed to an apparatus. The apparatus may include at least one processor and at least one memory including computer program code. The at least one memory and the computer program code may be configured, with the at least one processor, to cause the apparatus at least to obtain an electrical signal of a heart. The apparatus may also be caused to obtain a circulatory signal related to a pulsatile volume of blood in tissue. The apparatus may further be caused to preprocess the electrical signal and the circulatory signal. Further, the apparatus may be caused to train a mapping using the preprocessed electrical signal and circulatory signal. In addition, the apparatus may be caused to derive cardiovascular data based on the trained mapping of the preprocessed electrical signal or circulatory signal.

Other embodiments are directed to an apparatus. The apparatus may include means for obtaining an electrical signal of a heart. The apparatus may also include means for obtaining a circulatory signal related to a pulsatile volume of blood in tissue. The apparatus may further include means preprocessing the electrical signal and the circulatory signal. In addition, the apparatus may include means for training a mapping using the preprocessed electrical signal and circulatory signal. Further, the apparatus may include means for deriving cardiovascular data based on the trained mapping of the preprocessed electrical signal or circulatory signal.

Other embodiments are directed to a computer program, embodied on a non-transitory computer readable medium. The computer program, when executed by the processor, causes the processor to obtain an electrical signal of a heart. The method may also include obtaining a circulatory signal related to a pulsatile volume of blood in tissue. The processor is also caused to preprocess the electrical signal and the circulatory signal. In addition, the processor is caused to train a mapping using the preprocessed electrical signal and circulatory signal. Further, the processor is caused to derive cardiovascular data based on the trained mapping of the preprocessed electrical signal or circulatory signal.

BRIEF DESCRIPTION OF THE DRAWINGS

For proper understanding of example embodiments, reference should be made to the accompanying drawings, wherein:

FIG. 12(a) illustrates a confusion matrix for classification results on ground truth ECG signals using kernel SVM, according to certain embodiments.

FIG. 12(b) illustrates another confusion matrix for classification results on reconstructed ECG signals using kernel SVM, according to certain embodiments.

FIG. 12(c) illustrates a further confusion matrix for classification results on PPG signals using kernel SVM, according to certain embodiments.

DETAILED DESCRIPTION

It will be readily understood that the components of certain example embodiments, as generally described and illustrated in the figures herein, may be arranged and designed in a wide variety of different configurations. The following is a detailed description of some example embodiments of systems, methods, apparatuses, and computer program for reconstructing electrocardiogram (ECG) waveforms from photoplethysmogram (PPG).

The features, structures, or characteristics of example embodiments described throughout this specification may be combined in any suitable manner in one or more example embodiments. For example, the usage of the phrases "certain embodiments," "an example embodiment," "some embodiments," or other similar language, throughout this specification refers to the fact that a particular feature, structure, or characteristic described in connection with an embodiment may be included in at least one embodiment. Thus, appearances of the phrases "in certain embodiments," "an example embodiment," "in some embodiments," "in other embodiments," or other similar language, throughout this specification do not necessarily all refer to the same group of embodiments, and the described features, structures, or characteristics may be combined in any suitable manner in one or more example embodiments.

Additionally, if desired, the different functions or steps discussed below may be performed in a different order and/or concurrently with each other. Furthermore, if desired, one or more of the described functions or steps may be optional or may be combined. As such, the following description should be considered as merely illustrative of the principles and teachings of certain example embodiments, and not in limitation thereof.

Figure 1:
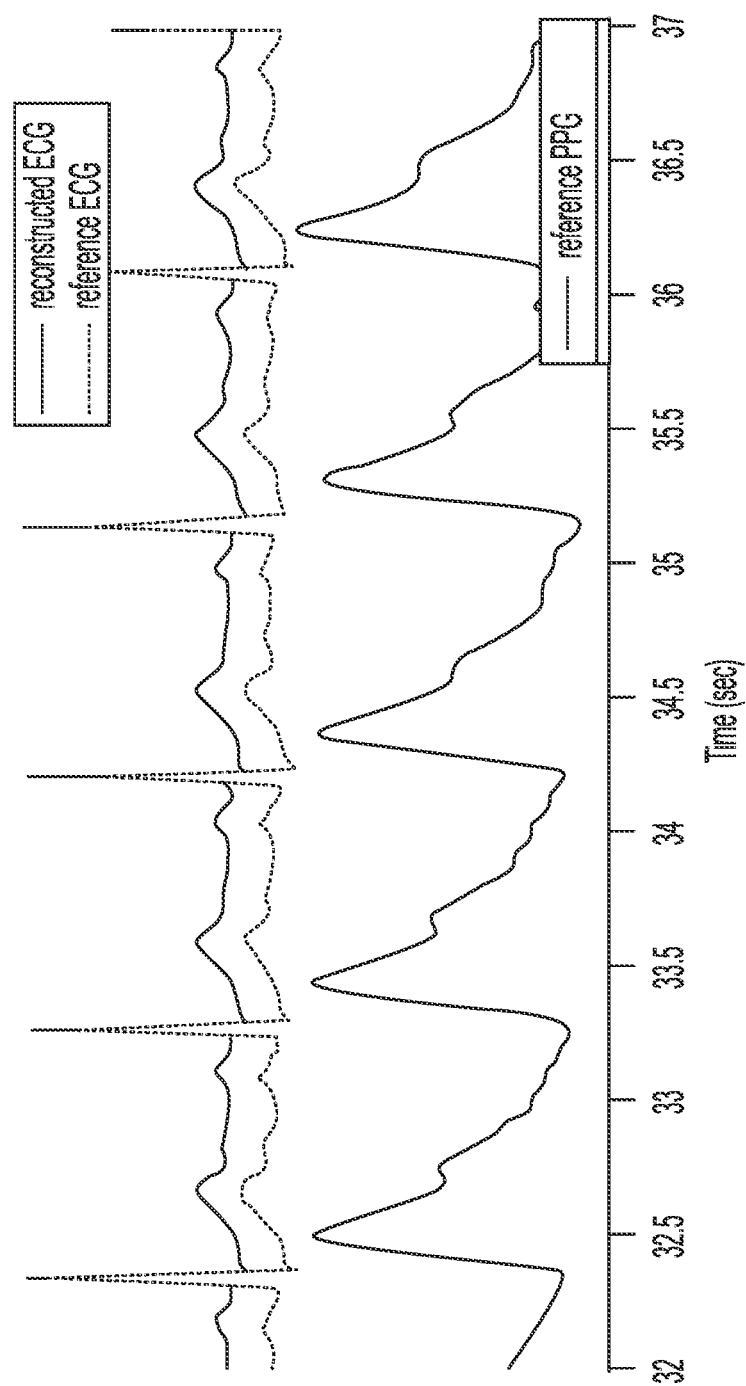
FIG. 1 illustrates a reconstructed electrocardiogram (ECG) signal, a reference ECG signal, and a reference photoplethysmogram (PPG) signal, according to certain embodiments.

FIG. 1 illustrates a reconstructed ECG signal, a reference ECG signal, and a reference PPG signal, according to certain embodiments. In particular, the top portion of FIG. 1 illustrates a five-second reconstructed ECG signal in a test set versus the reference ECG signal. As illustrated in FIG. 1, the two signals are intentionally drawn with an offset in the vertical direction to better reveal the details. Further, the lower portion of FIG. 1 illustrates the corresponding PPG signal used to reconstruct the ECG signal.

Certain embodiments may implement a machine learning method to train several classifiers to estimate ECG interval parameters from selected features of the PPG. Although certain systems may achieve approximately 90% accuracy on a benchmark hospital dataset, the capability confined to only estimating ECG parameters may restrict the direct deployment of the technology for ECG screening and monitoring.

According to certain embodiments, the waveform of the ECG signal may be estimated using PPG measurement by learning a signal model that relates the two time series. For example, as discussed in more detail herein, the ECG and PPG signal pairs may be processed to obtain temporally aligned and normalized sets of signals. The signals may then be segmented into pairs of cycles, and a linear transform may be trained to map the discrete cosine transform (DCT) coefficients of the PPG cycle to the DCT coefficients of the corresponding ECG cycle. The ECG waveform may then be obtained via the inverse DCT. In certain embodiments, the system may not be limited to use of the linear transform, and may also use a non-linear transform. For instance, in certain embodiments, a non-linear transform may be trained to map a component of the circulatory signal to a component of the electrical signal.

Figure 2:
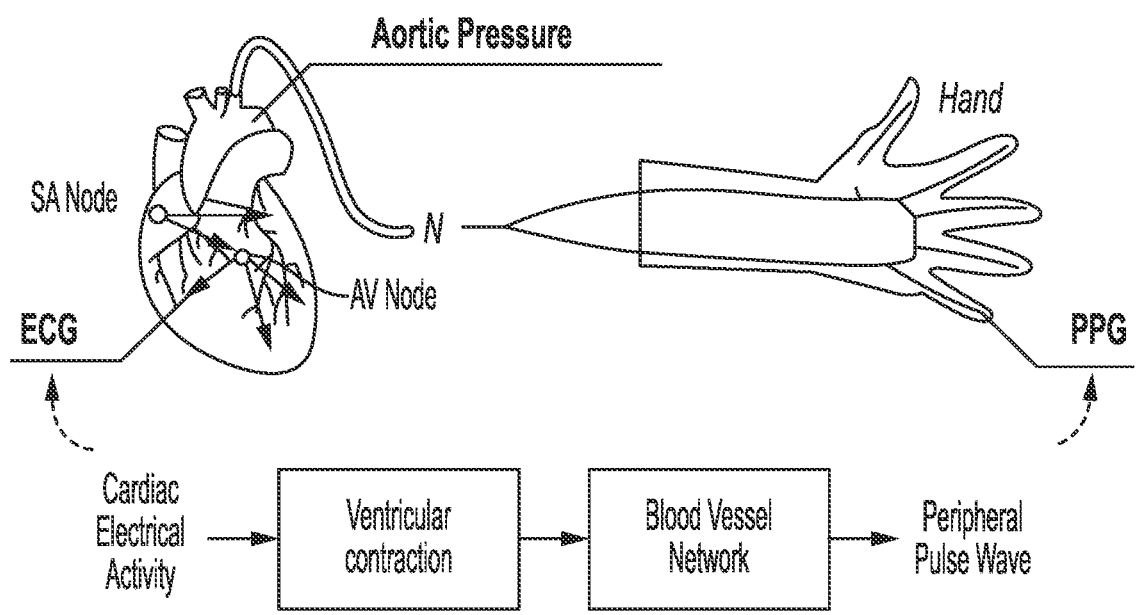
FIG. 2 illustrates a relationship between the ECG, the aortic pressure, and the PPG, according to certain embodiments.

FIG. 2 illustrates a relationship between the ECG, the aortic pressure, and the PPG, according to certain embodiments. As illustrated in FIG. 2, during each cardiac cycle, the atrioventricular (AV) node receives the electrical signals originated from the SA node. The AV node may then transmit this bio-electrical signal through the bundle of His, left bundle branches, and Purkinje fibers to the left ventricular myocardium, causing the depolarization and contraction of the left ventricle. As a result, the pressure of the left ventricle may rise and exceed the aortic pressure, causing the opening of the aortic valves, blood flow from the left ventricle into the aorta, and the corresponding rise of the aortic pressure. Upon release of the aortic valves, the generated pulse wave transmits the blood to the peripheral parts of the body, such as fingertips or toes, through a network of blood vessels.

Certain embodiments may consider the relationship between the ECG signal and the aortic pressure. For instance, in one specific cardiac cycle, a uniformly sampled cardiac electrical activity may be denoted $e(n)$, $n \in [1, L]$, where L is the total number of samples within the cycle. Further, the ECG measurement recording the potential difference between two electrodes placed on the surface of the skin of a person may be denoted as $c_y(n)$. In certain embodiments, taking into account the human body electrical resistance and the sensor noise, the ECG signal $c_y(n)$ may be modeled as:

$$c_y(n) = \alpha e(n) + v_y(n), \qquad (1)$$

where $\alpha$ denotes a subject-specific parameter accounting for the resistance of the electrical path between the heart and the skin surface, and $v_y(n)$ denotes the ECG sensor noise, which is modeled as a zero-mean white Gaussian process.

According to certain embodiments, the contraction and relaxation of the heart muscles follow the bio-electrical activities of the heart. These biomechanical activities further modulate the aortic pressure via the opening and closing of the aortic valves. The aortic pressure, denoted as $p_a(n)$, may thus be highly correlated with the cardiac electrical activities $e(n)$. In certain embodiments, this correlation may be modeled by first mapping both $e(n)$ and $p_a(n)$ to their frequency domain via type II DCT, as DCT has the potential to provide a compact and effective representation of the signals. Then, the relationship of the two signals may be modeled with a linear transform from the DCT domain of $e(n)$ to that of $p_a(n)$ as:

$$P_a = HE, \qquad (2)$$

where E, $P_a \in \mathbb{R}^{L \times 1}$ are the DCT-II coefficients of $e(n)$ and the aortic pressure $p_a(n)$ respectively. $H \in \mathbb{R}^{L \times L}$ is the transition matrix.

Certain embodiments may also correlate the pulse wave and the PPG signal. For instance, in certain embodiments, when the pulse wave and blood flow travel through the body from the aorta to a peripheral site, it may experience different interactions with the blood vessels, for instance, splitting and pushing. In certain embodiments, the structure of the blood vessel path of a specific person may be assumed as a time-invariant. As such, certain embodiments may model this blood vessel channel rom the aorta to the peripheral site as a linear time-invariant system. For instance, the peripheral pulse signal at a specific body site may be denoted as $p_p(n)$. In certain embodiments, $p_p(n)$ may be written according to the prior channel assumption as:

$$p_p(n) = b(n) \circledast p_a(n) + v_b(n), \qquad (3)$$

where $b(n)$ denotes the impulse response of the channel of blood vessels, and $\circledast$ denotes a symmetric convolution operation. According to certain embodiments, $v_b(n)$ is the zero-mean white Gaussian noise, capturing the variance of this model. The symmetric convolution of $b(n)$ and $p_a(n)$ may provide a result that is the same as a linear convolution of the symmetrically left-sided extended version of $b(n)$ and two-sided extended version of $p_a(n)$. Further, the extension of $p_a(n)$ may provide smooth boundary values for filtering near its original endpoints. According to certain embodiments, this "folded aliasing" may be preferable in modeling this blood vessel channel effect to the warp-around aliasing of a circular convolution.

In certain embodiments, the PPG sensor may be attached to the same peripheral site, and that the PPG sensor may work in the transmissive mode. That is, the photodetector of the PPG sensor may be on the other side of the tissue with the light-emitting diode. In addition, according to another embodiment, the light source may have a constant intensity of I on the spectral range of the receiver side, and it may be assumed that no relative motion between the attached skin and the photodetector is present, and that the contact is tight enough so that the signal is not influenced by the possible environmental illuminations. In an example embodiment, the PPG measurement denoted as $c_x(n)$, may be written as:

$$c_x(n) = I[\tau_0 + \tau_1 p_p(n)] + v_x(n), \qquad (4)$$

where $\tau_0$ and $\tau_1$ denote the relative transmissive strength of the non-pulsatile components and pulsatile components of tissue, respectively. Further, $v_x(n)$ denotes the PPG sensor noise, which may be modeled as a zero-mean white Gaussian process. Equation (4) may be rewritten as:

$$c_x(n) = I_1 p_p(n) + I_0 + v_x(n), \qquad (5)$$

where $I_1 = I\tau_1$ and $I_0 = I\tau_0$.

According to certain embodiments, an inverse model from PPG to ECG may be provided. For instance, in certain embodiments, according to the property of the symmetric convolution, a symmetric convolution in the time domain may be represented as a pointwise multiplication across the frequency domain of a cosine transform. Combined with the linearity property of the DCT, equation (3) may be rewritten in the frequency domain as:

$$P_p = BP_a + V_b, \qquad (6)$$

where $P_p$, $P_a$, and $V_b$ are the DCT-II coefficients of $p_p(n)$, $p_a(n)$, and $v_b(n)$ respectively. In addition, B diag($B_1$, $B_2$, ..., $B_L$)$\in \mathbb{R}^{L \times L}$, where $B_k$ denotes the kth DCT-I coefficient of $b(n)$. Next, a type II DCT may be applied on both sides of (1) and (5), which arrives at:

$$C_y = \alpha E + V_y \qquad (7)$$

$$C_x = I_1 P_p + I_0 + V_x, \qquad (8)$$

where $C_y$, $V_y$, $C_x$, $I_0$ and $V_x$ denotes the DCT-II coefficients of $c_y(n)$, $v_y(n)$, $c_x(n)$, constant function $I_0$ and $v_x(n)$, respectively. Assuming the nonsingularity of the matrix B and H and according to (2), (6), (7), and (8), the following may be obtained:

$$C_y = FC_x + C_0 + V, \qquad (9)$$

where $F \triangleq \alpha I_1^{-1} H^{31} \ ^1B^{-1}$, $C_0 \triangleq \alpha I_1^{-1} H^{-1} B^{-1} I_0$, and $V \triangleq V_y \alpha H^{-1} B^{-1} (I_1^{-1} V_x + V_b)$. When each element of $C_y$ is looked at individually, the following may be obtained:

$$C_y(k) = F(k) C_x + C_0(k) + V(k), \ k \in [1, L], \qquad (10)$$

where $F(k)$ is the kth row of matrix F; $C_0(k)$ and $V(k)$ denote the kth element of $C_0$ and V, respectively. In certain embodiments, $V(k)$ may be known as a zero-mean Gaussian random variable, as it is a linear combination of zero-mean Gaussian random variables from $v_y$, $v_b$, and $v_x$. According to equation (10), the relation between the PPG and the ECG signal may be captured by a linear model in their frequency domain.

Thus, there exists certain linear relationships between the DCT coefficients of PPG signal and those of the ECG signals.

Figure 3:
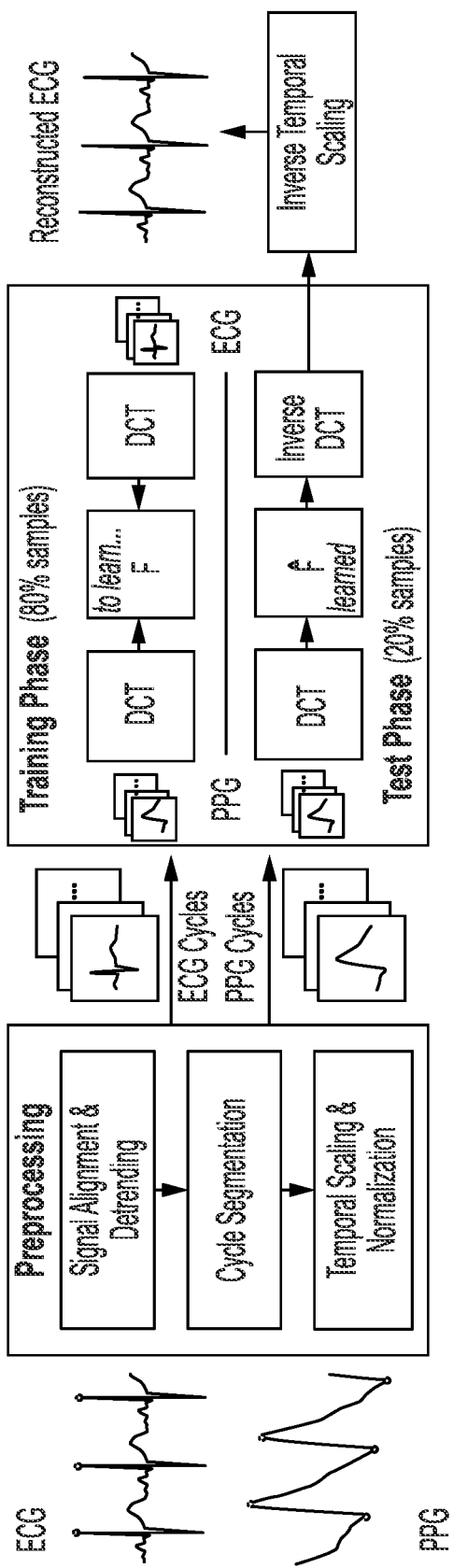
FIG. 3 illustrates a flowchart of a system, according to certain embodiments.
Figure 4A:
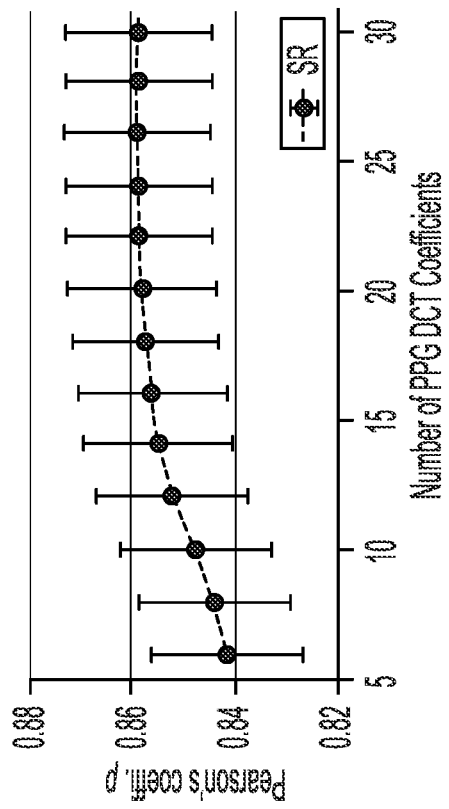
FIGS. 4(a)-(h) illustrate line plots of the performance of the system in a test set using either an SR segmentation scheme or an R2R segmentation scheme, according to certain embodiments.
Figure 4B:
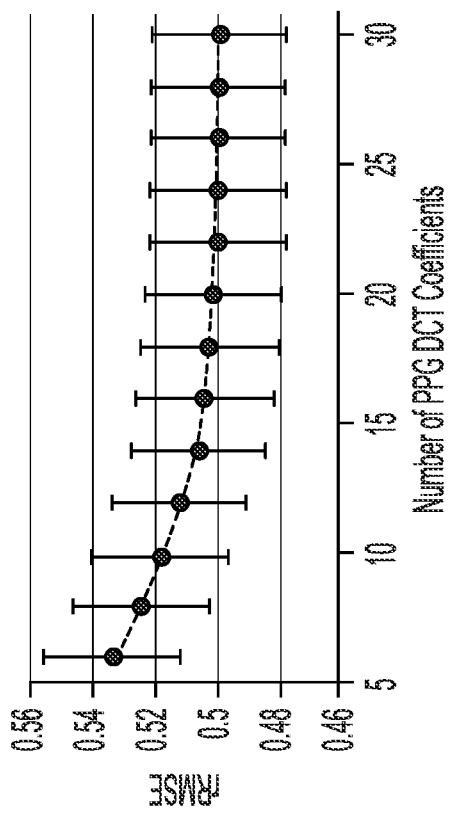
Figure 4C:
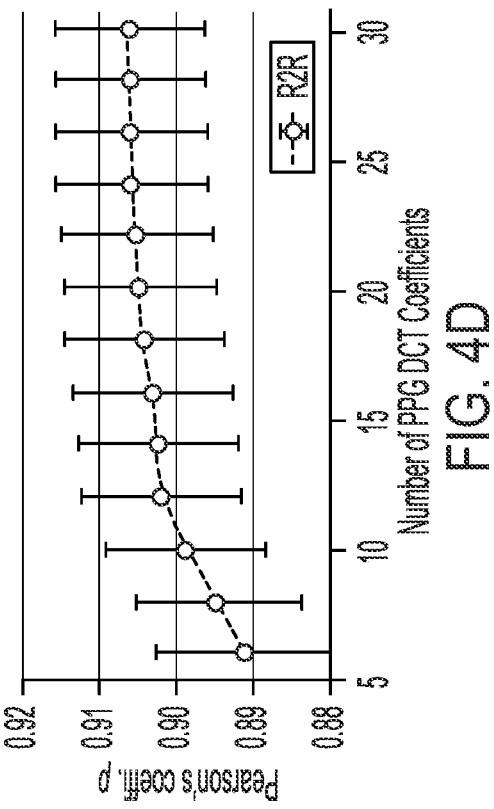
Figure 4D:
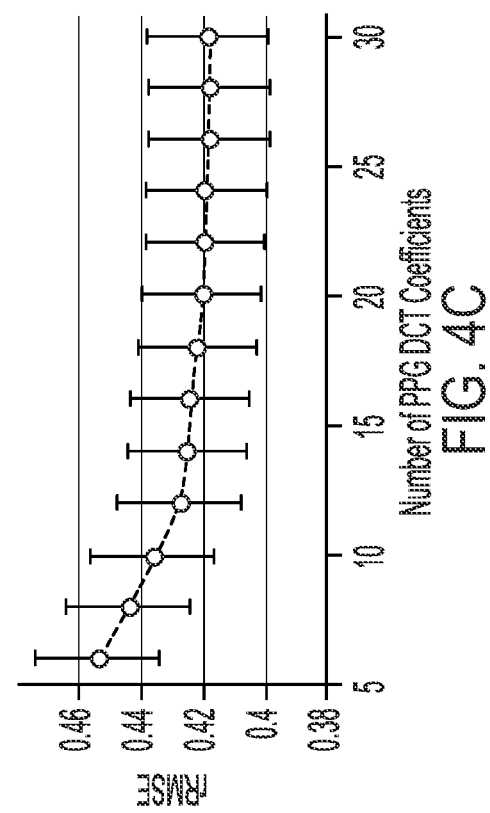
Figure 4E:
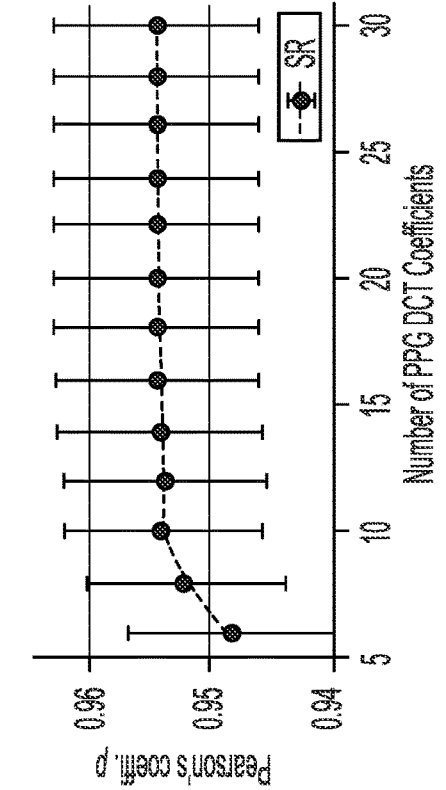
Figure 4F:
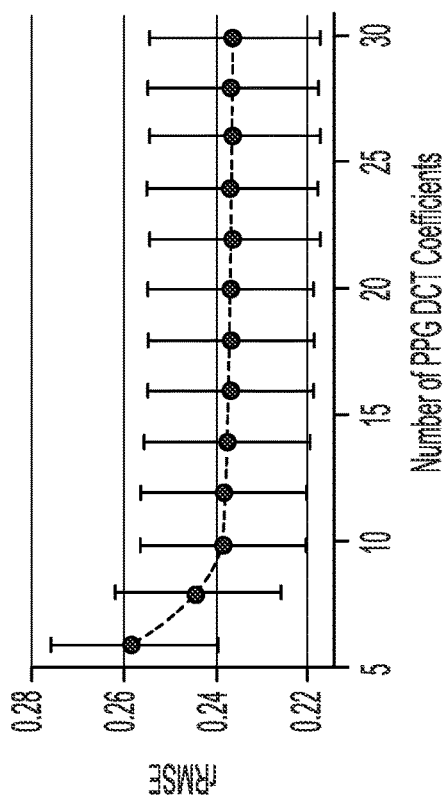
Figure 4G:
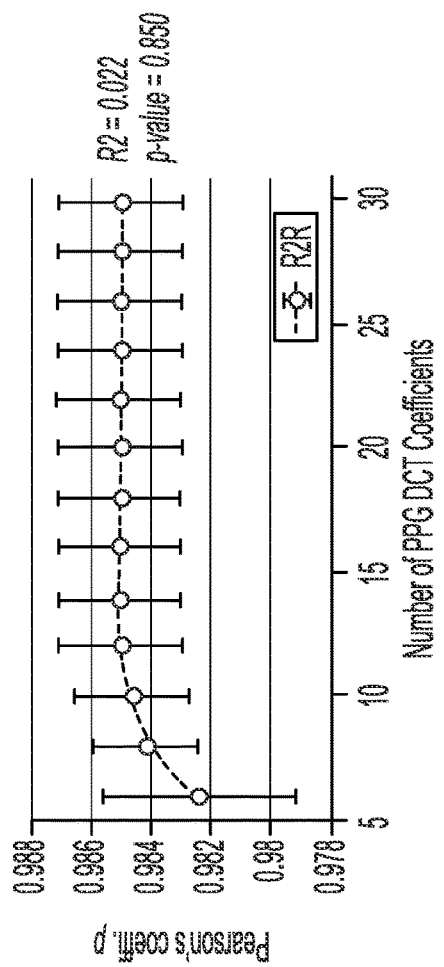
Figure 4H:
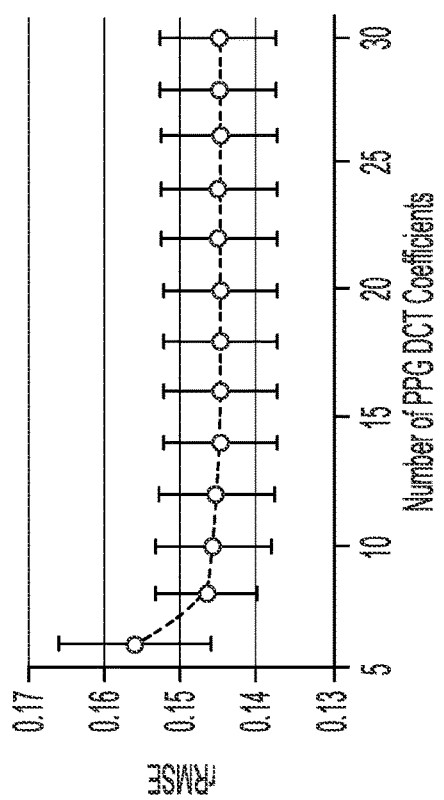

FIG. 3 illustrates a flowchart of a system, according to certain embodiments. In certain embodiments, a system may be provided that learns the linear transform F from pairs of PPG and ECG data. The pipeline of the system is illustrated in FIG. 3, where the ECG and PPG signals are first preprocessed to obtain physically aligned and normalized pairs of cycles. The selected DCT coefficients of 80% pairs of cycles may be used for training a linear transform F, which may be used in the test phase to reconstruct the ECG signals. After preprocessing, the cycle pairs may be fed into the training system to learn the transform matrix.

According to certain embodiments, the preprocessing stage may include cycle-wise segmentation. In certain embodiments, preprocessing ECG and PPG signals may obtain temporally aligned and normalized pair of signals so that the critical temporal features of both waveforms may be sufficiently captured.

In cycle-wise segmentation, the ECG and PPG signals may be preprocessed to obtain temporally aligned and normalized pairs of the signal cycles to facilitate the investigation in the subsequent training stage. For instance, the left part of FIG. 3 illustrates the preprocessing phase, which includes data alignment, signal detrending, cycle-wise segmentation, temporal scaling, and normalization stages.

In data alignment and detrending, as the relation between ECG and PPG is modeled in the cycle level, the signal delay may be estimated in each trail, and the signals may be temporally aligned. To achieve this, a two-level signal alignment scheme may be provided. For instance, the peak features of the signal pair may be used to estimate the cycle-wise delay. The peak features in this case may generally refer to the R peak of the ECG signal and the systolic peak of the PPG signal. Then, the pair of ECG and PPG signals may be aligned to the sample level based on the physical meaning and correspondence of the two signals. Here, both ECG and PPG signals may be discrete time signals (sampled in time). For instance, the sample may refer to the temporal sampled measurement of the ECG and PPG signals. In addition, the signal may be coarsely aligned in the signal's cycle level and then alignment may be refined to the sample level within the aligned cycle.

According certain embodiments, a pair of almost simultaneously recorded PPG and ECG signals may be provided. This pair may be denoted as $x \in \mathbb{R}^T$ and $y \in \mathbb{R}^T$, respectively. In certain embodiments, the coordinate of the systolic peak in the ith cycle of PPG may be $n_{sp}(i)$, and the R peak of ECG may be $n_{rp}(i)$. In another embodiment, the cycle delay $m_{delay}$ may be searched for in a discrete interval $D \triangleq [-k, k]$. Further, for each evaluated $m \in \mathbb{D}$, the signal may be preliminarily aligned with respect to $n_{sp}(1-m \cdot \mathbb{1}(m>0))$, and $n_{rp}(1-m \cdot \mathbb{1}(m>0))$. In addition, the aligned coordinates of PPG and ECG peaks are $\{n'_{sp}(m)\}$ and $\{n'_{rp}(m)\}$, and the cycle delay $\hat{m}_{delay}$ may be estimated by solving the following problem:

$$\hat{m}_{delay} = \underset{m \in D}{\arg\min} \sum_{i=1}^{i=M-k} |n'_{sp}(i - m \cdot \mathbb{1}(m<0)) - n'_{rp}(i + m \cdot \mathbb{1}(m>0))|, \quad (11)$$

where M denotes the total number of cycles, and $\mathbb{1}$ denotes the indicator function. After the cycle delay $\hat{m}_{delay}$ is estimated, the PPG signals are shifted so that the systolic peaks of PPG and the R peaks of ECG are temporally matched.

In certain embodiments, the R peak of the ECG and the onset point of PPG may be aligned in the same cycle, considering that the R peak corresponds approximately to the opening of the aortic valve, and the onset point of PPG indicates the arrival of the pulse wave. In this way, the PPG and ECG signals may be aligned within the cycle according to their physiological correspondence.

According to certain embodiments, quasi-DC components in both signals caused by respiration, vasomotor activity, and thermoregulation may require additional attention to temporal pattern analysis. With the prior information that such non-stationarities represent slowly-varying trends in the signal (original signal), the trends from the ECG and PPG signals may be estimated using the smooth method and subtract the trends from the original signals. In certain embodiments, the original signals may correspond to the same signals of the ECG and PPG measured prior to the preprocessing stage. In another embodiment, the original signal may include a slowly-varying trend. The smoothing method may be applied to estimate the trend in the original signal, and the trend may be subtracted from the original signal. In addition, the trend may be assumed to be a smooth, unknown version of the original signal with a property that its accumulated convexity measured for every point on the signal is as small as possible. The trend may then be estimated using a regularized least square method.

As previously noted, the preprocessing may also include segmentation and normalization. According to certain embodiments, each cycle of the signal $\tilde{x}$ and $\tilde{y}$ may be segmented to prepare for the learning phase. In certain embodiments, two cycle segmentation schemes may be provided, which may include an SR segmentation scheme in segmenting PPG and ECG signals and R peak-to-R peak (R2R) segmentation scheme. In SR, the signal may be segmented according to the points that are ⅓ of the cycle length to the left of the R peaks of the ECG signal. This scheme is called SR as it approximately captures the standard shape of sinus rhythm. On the other hand, in R2R, the signal is segmented according to the location of the R peak of the ECG signal to mitigate the reconstruction error in the QRS complex. After segmentation, each cycle sample may be scaled in time and amplitude to make it of equal length L, zero mean, and unit sample standard deviation. In certain embodiments, the normalized PPG and ECG cycle samples may be denoted as: $c_x, c_y \in \mathbb{R}^{M \times L}$.

Further, certain embodiments may learn a DCT-domain linear transform. For example, the right part of FIG. 3 illustrates a learning framework, according to certain embodiments. The linear transform F in the signal model (10) may be learned in the training phase, and may be used to reconstruct the ECG waveform in the test phase. Specifically, a cycle-wise DCT may be performed on $c_x$ and $c_y$, which yields $C_x, C_y \in \mathbb{R}^{M \times L}$. Then, the first $L_x, L_y$ DCT coefficients of $C_x, C_y$ may be selected to represent the corresponding waveform as the signal energy is concentrated mostly on the lower frequency components. In certain embodiments, the coefficients may be denoted as $\widetilde{C_x} \in \mathbb{R}^{M \times L_x}$ and $\widetilde{C_x} \in \mathbb{R}^{M \times L_y}$. Next, $\tilde{C}_x$ and $\tilde{C}_y$ may be separated into training and test sets as $C_{x,train} \in \mathbb{R}^{M_{train} \times L_x}$, $C_{y,train} \in \mathbb{R}^{M_{train} \times L_y}$, and $C_{x,test} \in \mathbb{R}^{M_{test} \times L_x}$, $C_{y,test} \in \mathbb{R}^{M_{test} \times L_y}$, where $M_{train} + M_{test} = M$.

According to certain embodiments, in the training process, the linear transform matrix $F^* \in \mathbb{R}^{L_x \times L_y}$ may be learned that maps from PPG to ECG DCT coefficients using three least square methods. These methods may include ordinary least square (OLS), ridge regression (ridge), and least absolute shrinkage and selection operator (lasso).

In certain embodiments, the OLS solution of F may be the minimizer of residue sum-of-squares of the ECG DCT coefficients:

$$F^*_{OLS} = \underset{F}{\operatorname{argmin}} \|C_{x,train}F - C_{y,train}\|_F^2, \quad (12)$$

where $\|*\|_F$ denotes the Frobenius norm of a matrix. Further, the OLS may generate the most straightforward closed-form solution $F^*_{OLS} = (C_{x,train}^T C_{x,train})^{-1} C_{x,train}^T C_{y,train}$ with low prediction bias, but its estimates often have large prediction variance. In addition, according to certain embodiments, prediction accuracy may be improved by regularized least square methods, such as the ridge and lasso.

According to certain embodiments, the ridge may add a regularization term after the OLS formulation to shrink the size of F. For instance, the ridge estimate may be defined by:

$$F^*_{ridge} = \underset{F}{\operatorname{argmin}} \|C_{x,train}F - C_{y,train}\|_F^2 + \gamma \|F\|_F^2, \quad (13)$$

where $\gamma > 0$ is a complexity parameter that controls the shrinkage of F toward zero thereby reducing the variance of the predictions. The analytic solution to (13) is $F^*_{ridge} = (C_{x,train}^T C_{x,train} + \gamma I)^{-1} C_{x,train}^T C_{y,train}$, where I is the identity matrix.

The lasso is another shrinkage method similar to ridge, but replaces the penalty $\|F\|_F^2$ with $\|F\|_1$. This subtle difference may lead to a completely different solution with the "soft thresholding" of the entries in $F_{lasso}$ and, thus, may give high interpretability of the model. According to certain embodiments, the lasso with the alternating direction method of multipliers may be solved.

According to certain embodiments, n the test phase, the optimal linear transform F* may be applied, which was learned in the training stage on $C_{x,test}$ and estimate the corresponding DCT coefficients of ECG cycles. The estimate may be denoted as $\hat{C}_{y,test} \triangleq C_{x,test} F^*$. To reconstruct ECG, each row of $\hat{C}_{y,test}$ may be augmented to be in the same dimension as L (by padding zeros). The zero-padded matrix may be denoted as $\tilde{\hat{C}}_{y,test} \in \mathbb{R}^{M_{test} \times L}$. Then, the inverse DCT may be applied to each row of $\tilde{\hat{C}}_{y,test}$, the resulted matrix may be interpolated row by row to its original temporal scale, and the inversely scaled pieces of the cycles may be concatenated to obtain the reconstructed ECG signal $\hat{y}_{test}$.

EXPERIMENTS

Experiment 1: Capnobase TBME-RR Database

According to certain embodiments, various experiments may be conducted. For example, a first experiment may relate to Capnobase IEEE Transactions on Biomedical Engineering Photoplethysmography Respiration Rate (TBME-RR) database. In particular, the Capnobase TBME-RR may be used to evaluate the performance of the systems. The dataset may include 42 eight-min sessions of simultaneously recorded PPG and ECG measurements from 29 pediatric and 13 adults, sampled at 300 Hz. The 42 cases were randomly selected from a larger collection of physiological signals collected during elective surgery and routine anesthesia. Each recorded session corresponds to a unique subject, and the PPG signal was acquired on subjects' fingertips via a pulse oximeter. The dataset had a variety of patient's age and weight (min: 9 kg, max: 145 kg, median: 49 kg), and is thus a favorable dataset for testing the performance of the system.

In the first experiment, the signals were pruned according to the human-labeled artifact segments and processed the pairs of ECG and PPG signal using the method introduced above to obtain aligned and normalized pairs of the signal cycles. Further, L=300 and $L_y$=100 was set, as most of the diagnostic information of EC was contained below 100 Hz. In addition, $\lambda$=500 and $\gamma$=10 was set empirically as they offer the best regularization results in the tasks. In order to test the consistency of the system, the first 80% of each session was selected as the training set and the rest for testing. The following two metrics were used to evaluate the system performance in the test set:

Relative root mean squared error:

$$rR_{MSE}(y_{test}, \hat{y}_{test}) = \frac{\|y_{test} - \hat{y}_{test}\|_2}{\|y_{test}\|_2}, \quad (14)$$

Pearson's correlation coefficient:

$$\rho(y_{test}, \hat{y}_{test}) = \frac{(y_{test} - \bar{y}_{test})^T (\hat{y}_{test} - \bar{\hat{y}}_{test})}{\|y_{test} - \bar{y}_{test}\|_2 \|\hat{y}_{test} - \bar{\hat{y}}_{test}\|_2}, \quad (15)$$

where $y_{test}$, $\hat{y}_{test}$, and $\bar{y}_{test}$ denote the ECG signal in the test set, the average of all coordinates of the vectors, $\hat{y}_{test}$, and $y_{test}$, respectively.

In the first experiment, the system was evaluated in two different training modes: subject independent (SI) mode and subject dependent (SD) mode. In SI mode, a single linear transform F* was trained using all the training data. This included, for example, the trained model that is independent with each subject in the dataset. In SD mode, a linear transform F* was trained and tested in each session. In this way, an SD model may be obtained for each individual.

In certain embodiments, the number of DCT coefficients of the PPG signal $L_x$ were cross-validated and used in the learning system. According to certain embodiments, the more variables that were used as predictors (i.e., more PPG DCT coefficients used in the linear system), the better the performance can be achieved in training. However, it can be observed from FIGS. 4(a)-(h) that the performance of the system in the test set using either SR and R2R becomes saturated as $L_x$ gets more significant from approximately 18 and 12 in the SI and SD mode, respectively. As illustrated in FIG. 4, the line plots give the average of $rR_{MSE}$ in (a), (c), (e), and (g) and $\rho$ in (b), (d), f), and (h) of all sessions in the test set for different choices of number of PPG DCT coefficient $m_1$ using SR (a), (b), (e), and (h) and R2R (c), (d), (g), and (h) segmentation scheme and SI (a)-(d) and SD (e)-(h) mode, respectively. In addition, FIG. 4 illustrates that the vertical bars at each data point shows one standard error above and below the sample mean. The trends of convergence in both modes suggest potential model overfitting. In addition, another observation is that the convergence rate is slower in the SI mode compared with the SD mode. Such observation is expected because the data diversity is much higher in the SI mode than that in the SD mode, and more variables are needed to capture the additional variance in the SI mode. $L_x=18$ in the SI mode and $L_x=12$ in the SD mode are thus favorable, as the system has comparable performance and the model is parsimonious than those with larger $L_x$.

Figure 5:
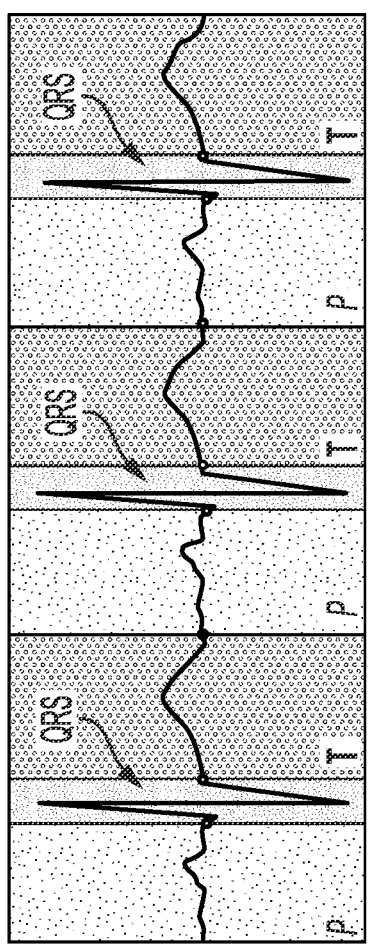
FIG. 5 illustrates an example of ECG segmentation result on three cycles of the ECG signal in the first session of an IEEE Transactions on Biomedical Engineering Photoplethysmography Respiratory Rate Benchmark Dataset (TBME-RR), according to certain embodiments.

The norm of one cycle of ECG signal may be dominated by that of QRS complex. This fact of unbalanced signal energy distribution may lead to insufficient evaluation on the P wave and T wave of the ECG signal. Thus, to address this problem, the ECG cycle was further separated into a P-wave, QRS-complex, and a T-wave for more detailed evaluation, and the system performance was evaluated on segments of the P-wave, QRS-wave, and T-wave. The evaluation was performed in terms of rRMSE and $\rho$ on each segment as well as using the entire cycle of the signal. Specifically, the QRS detection algorithm was adopted to locate the onset and endpoint of the QRS complex. The 60% point was empirically selected between the onset points of two adjacent QRS complexes as the separating point for the P and T wave. FIG. 5 illustrates an example of the ECG segmentation result on three cycles of the ECG signal in the first session of TBME-RR database, according to certain embodiments. Specifically, FIG. 5 illustrates an example of the ECG segmentation result sampled from the first subject in the database. It is noted that the onset and endpoint of all waves in each cycle were accurately estimated. As illustrated in FIG. 5, the different sections of the plot denote the estimated P waves, the QRS waves, and the T waves, respectively. In addition, for each cycle, the ratio between the duration of the QRS+T wave is about 3/2 of the duration of the T wave.

Figure 6A:
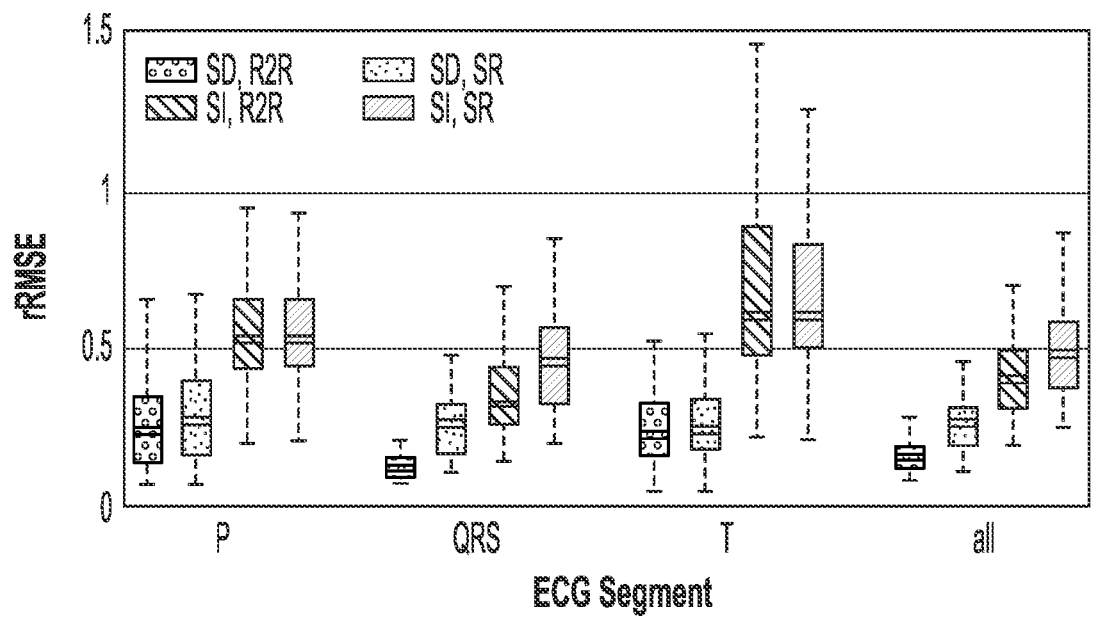
FIG. 6(a) illustrates a comparison of the performance of a method in a test set of the TBME-RR database in different combinations of SR or R2R segmentation schemes, and the subject dependent (SD) or subject independent (SI) test modes evaluated at P, QRS, T, and all waves, according to certain embodiments.
Figure 6B:
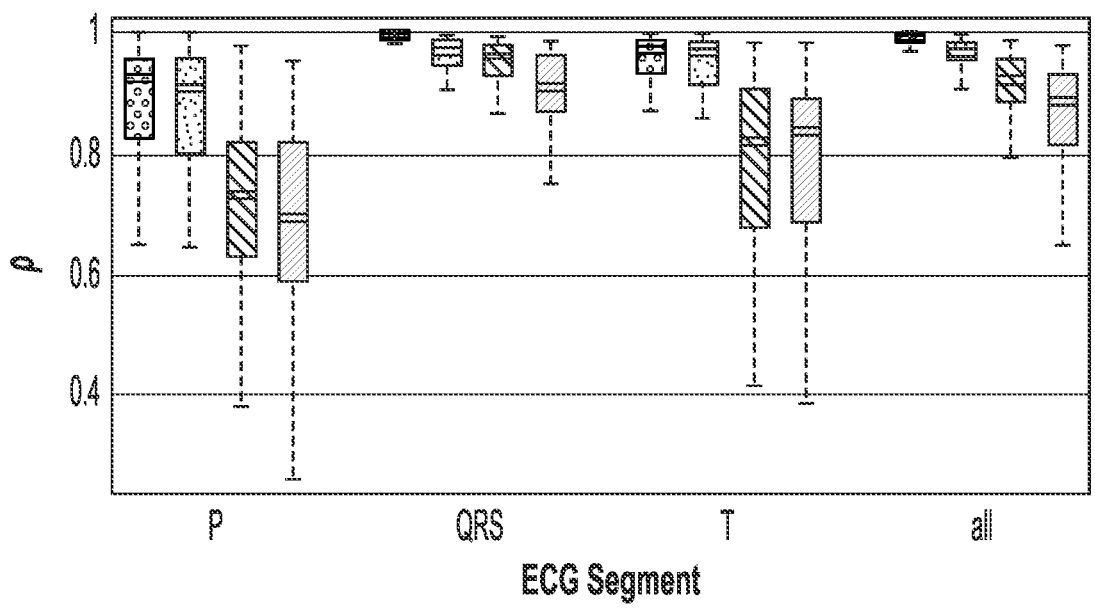
FIG. 6(b) illustrates another comparison of the performance of the method in a test set of the TBME-RR database in different combinations of SR or R2R segmentation schemes, and the SD or SI test modes evaluated at P, QRS, T, and all waves, according to certain embodiments.

FIGS. 7(a) and 7(b) illustrate box plots of the results using R2R and SR segmentation schemes in different training modes. In particular, FIGS. 7(a) and 7(b) illustrate a comparison of the performance of the method in a test set of the TBME-RR database in different combinations of the SR or R2R segmentation schemes and the SD or SI test modes evaluated at P, QRS, T, and all waves. Specifically, FIG. 6(a) illustrates statistics of the rRMSE, and FIG. 6(b) illustrates $\rho$ summarized using box plots.

In certain embodiments, it was found that overall R2R gives better performance than SR, and model trained in the SD mode gives better performance compared with that trained in the SI mode in this dataset as possible subject differences in terms of H in (2) and b(t) in (3) are expected. The three regression methods, OLS, ridge and lasso give comparable performance. In general, R2R outputs comparable results on P and T waves compared with SR, whereas R2R outperforms SR on QRS and all waves. In the SD mode, the average performance in $\rho$ on T wave was about 0.92 using R2R and 0.90 using SR, much higher values than those on the P wave. According to certain embodiments, there may be two possible reasons that explain this result. First, compared with the QRS and T waves, the amplitude of the P wave is much smaller. As a result, the P wave becomes more sensitive to the noise compared with the T wave. Second, the shape of the T wave signifies the repolarization of the ventricles, and the ventricular repolarization is correlated with the shape of the dicrotic notch in the PPG signal. This is because, during the ventricular repolarization process, the closure of the aortic valve is associated with a small backflow of blood into the ventricle and a characteristic notch in the aortic pressure tracings. This connection between the P wave of ECG and the dicrotic notch of PPG may facilitate the system performance on the P wave.

Figure 7:
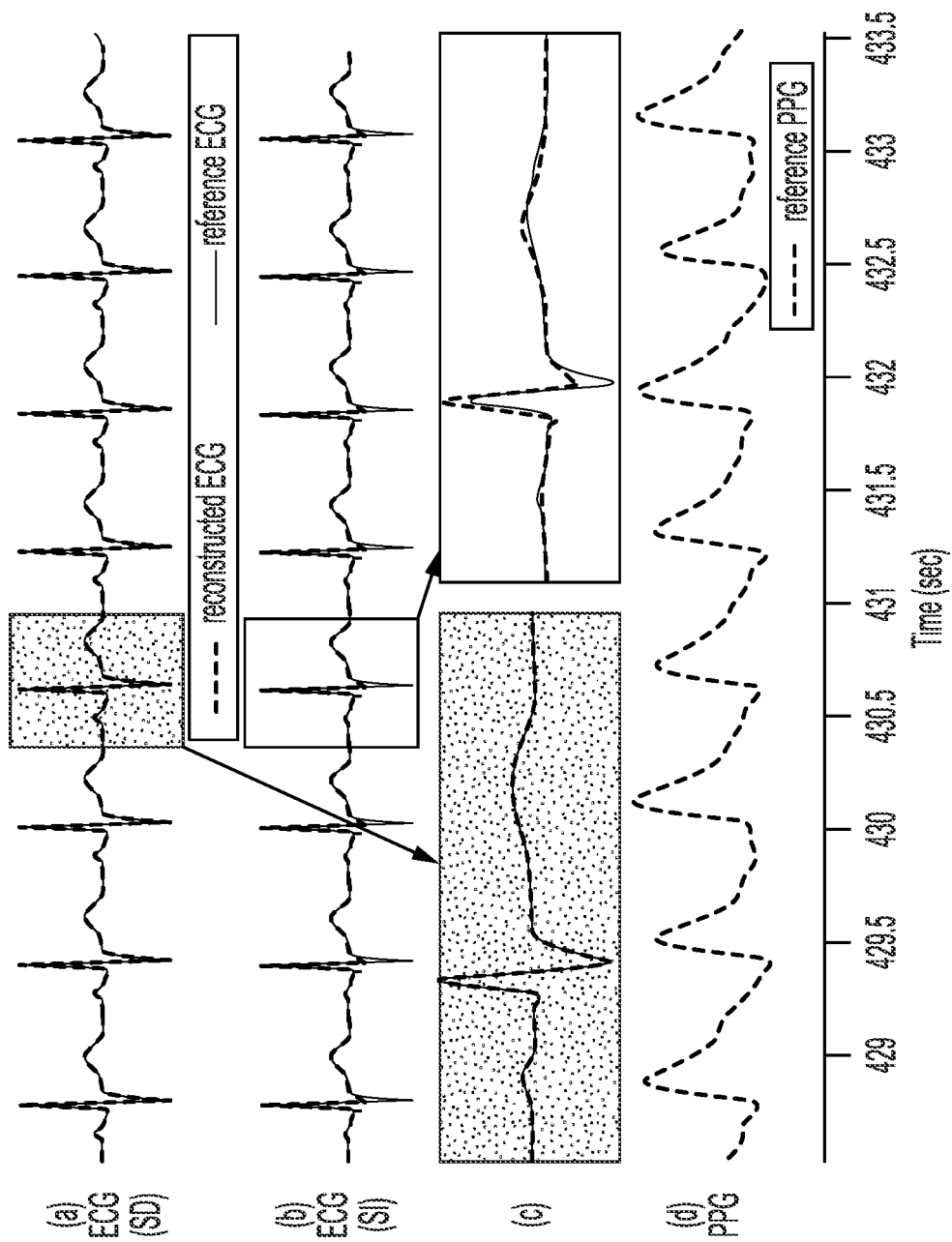
FIG. 7 illustrates a five-second segment of the reconstructed ECG waveform in the test set of the first subject using the R2R cycle segmentation scheme, according to certain embodiments.

As an example, FIG. 7 illustrates a five-second segment of the reconstructed ECG waveform in the test set of the first subject using the R2R cycle segmentation scheme with $L_x=18$ in the SI mode and $L_x=12$ in the SD mode, according to certain embodiments. As illustrated in FIG. 7, the reconstructed ECG (solid line) in (a) the SD and (b) SI and the reference ECG (dashed line) waveform of the last 5 seconds of the first session (age: 4 years old, weight: 18 kg) in TBME-RR database. Zoomed-in version of the shaded cycle in each mode is also illustrated in (c), and the corresponding PPG waveform is illustrated in (d). Furthermore, in this experiment, the first subject was selected to be the example as the system performance evaluated on this subject approximates the average performance over the database. It can be seen from the plot that the system retains most of the shape of the original ECG waveform except for the S peaks in the SI mode and almost perfectly reconstructs the ECG waveform and maintains the location of each PQRST peaks in the SD mode.

FIGS. 8(a)-(d) illustrate plots of rRMSE and $\rho$ of each session concerning subjects' age and weight, respectively in two 3-D plots n the SI and SD mode. As illustrated in FIGS. 8(a)-(d), a linear model is fit with an interaction term for each combination of training mode and evaluation metric according to the least-squares criterion. An F-test was performed to test whether subjects' profile, i.e., age, weight, and the interaction between age and weight, can significantly affect the performance of the algorithm in each metric and training mode combination. F-test results of small p-values shown in FIGS. 8(a) and 8(b) for the SI mode reveal that the performance of the algorithm is dependent on the combination of the subject's age and weight, whereas the large high p-values shown in FIGS. 8(c) and 8(d) for the SD mode does not show a strong evidence to reject the hypothesis that the performance of the algorithm is independent of age and weight. Moreover, the performance tends to be lower as the subject's weight gets larger. This trend of performance degradation may be due to the bias of the training sample that the number of newborns is much larger than the number of other groups of subjects in the database.

Figure 8A:
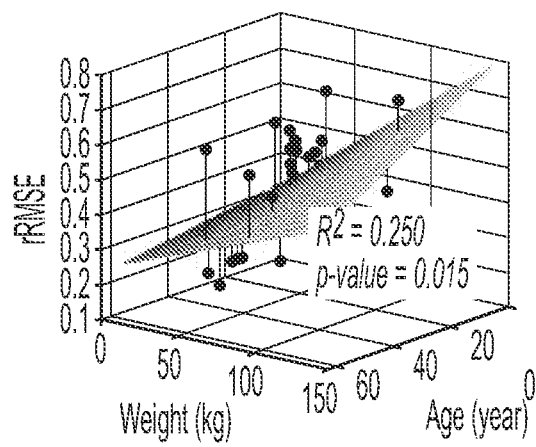
FIG. 8(a) illustrates a relative root mean square error (rRMSE) versus subjects' weight and wage in SI mode, according to certain embodiments.
Figure 8B:
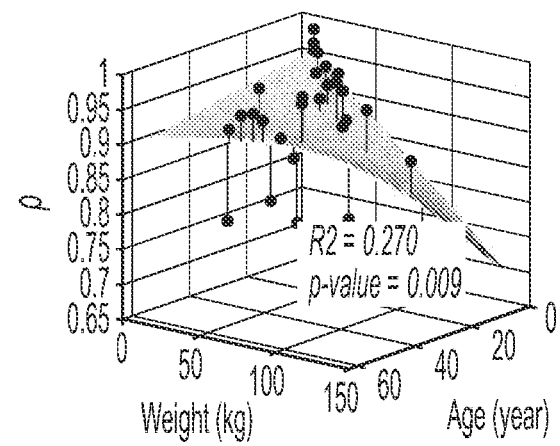
FIG. 8(b) illustrates ρ versus subjects' weight and age in SI mode, according to certain embodiments.
Figure 8C:
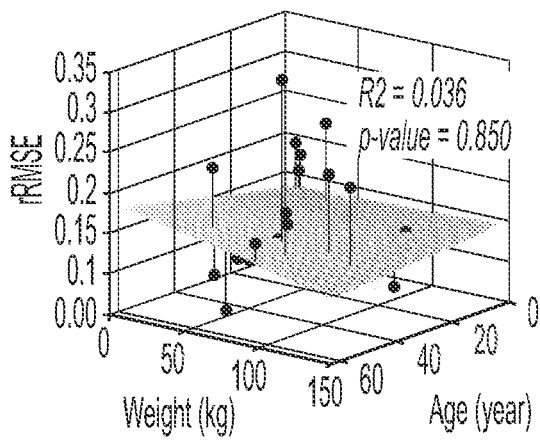
FIG. 8(c) illustrates a rRMSE versus subjects' weight and age in SD mode, according to certain embodiments.
Figure 8D:
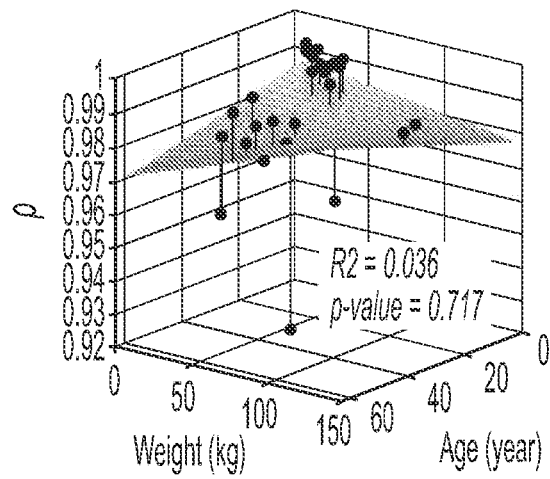
FIG. 8(d) illustrates ρ versus subjects' weight and age in SD mode, according to certain embodiments.

Furthermore, the scatter plots of FIG. 8(a) relates to rRMSE and FIG. 8(b) relates to $\rho$ vs. subjects' weight and age using R2R scheme. Each sample corresponds to one of 42 sessions. In addition, the surface mesh on each plot shows the regressed linear model: rRMSE or $\rho$~intercept+age+weight. Further, the $R^2$ and the p-value of F-test is shown in each plot.

Experiment 2: MIMIC-III Database

Medical information mart for intensive care III (MIMIC-III) is an extensive database including vital sign measurements at the bedside documented in MIMIC-III waveform database and part of the patients' profile in the MIMIC-III clinical database. The database encompasses a large population of ICU patients. In this experiment, a subset of the MIMIC-III database was used to evaluate the system's performance when the subjects were with various cardiac or non-cardiac malfunctions.

Figure 9:
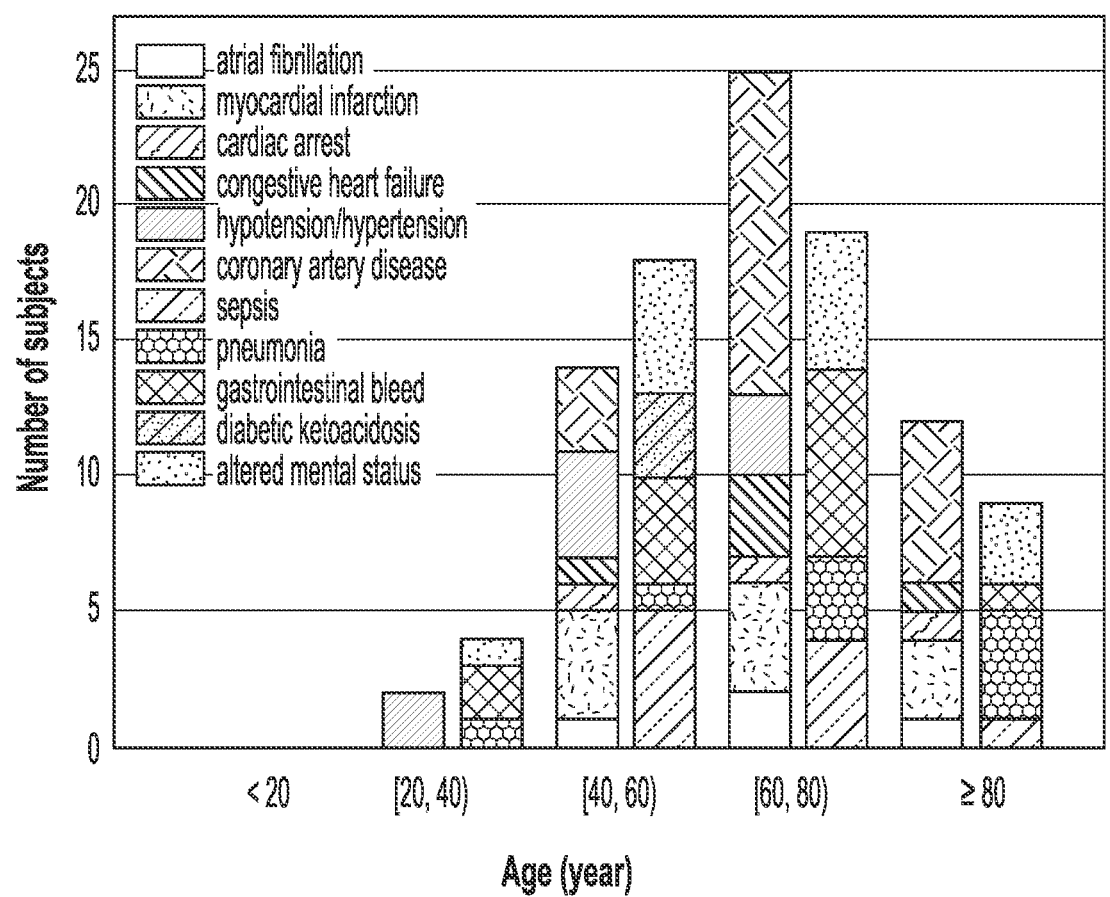
FIG. 9 illustrates a distribution of subjects collected from a medical information mart for intensive care III (MIMIC-III) database in five age groups and eleven disease types, according to certain embodiments.

Specifically, waveforms that contain both lead II ECG and PPG signals from folder 35 in the MIMIC-III waveform database were selected. Then, the selected waveforms were linked with the MIMIC-III clinical database by subject ID to match with the corresponding patient profile. Among the patients, those with specific cardiac/non-cardiac diseases were selected, and those with low signal quality PPG/ECG pairs were removed. The resulting collected database consists of 53 patients with six common cardiac diseases, and 50 patients with five types of non-cardiac diseases. The distribution of the collected patients was visualized in stacked bar plot based on each one's age group and disease type in FIG. 9. As illustrated in FIG. 9, distributions of subjects were collected from the MIMIC-III database in five age groups and eleven disease types. Within each age group, the cardiac-related diseases and noncardiac-related diseases are colored as different shades.

Furthermore, each patient has three sessions of 5-min ECG and PPG recordings collected within several hours. Cardiac diseases in the resulting database include atrial fibrillation, myocardial infarction, cardiac arrest, congestive heart failure, hypotension, hypertension and coronary artery disease, while non-cardiac diseases are composed of sepsis, pneumonia, gastrointestinal bleed, diabetic ketoacidosis and altered mental status. In this part of the experiment, the system was evaluated in the following two training modes (both under R2R segmentation scheme). The first mode is SI mode where one linear transform F* was trained using training data from patients with cardiac diseases, and another linear transform F* was trained from non-cardiac disease patients (i.e., the trained model was independent with each subject in terms of disease type. The second mode was SD mode, where for each subject, a linear transform F* was trained on the first two sessions and tested on the third session. In this way, it was possible to obtain a subject dependent model for each individual.

Figure 10A:
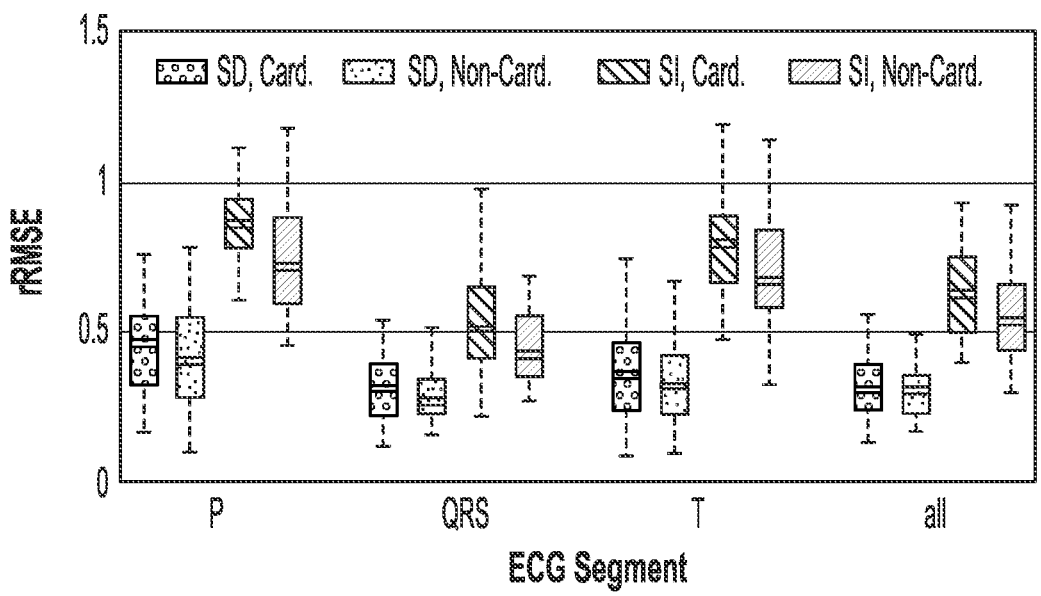
FIG. 10(a) illustrates a comparison of the performance of a method in test set of the MIMIC-III database in different combinations of the disease types and test modes, according to certain embodiments.
Figure 10B:
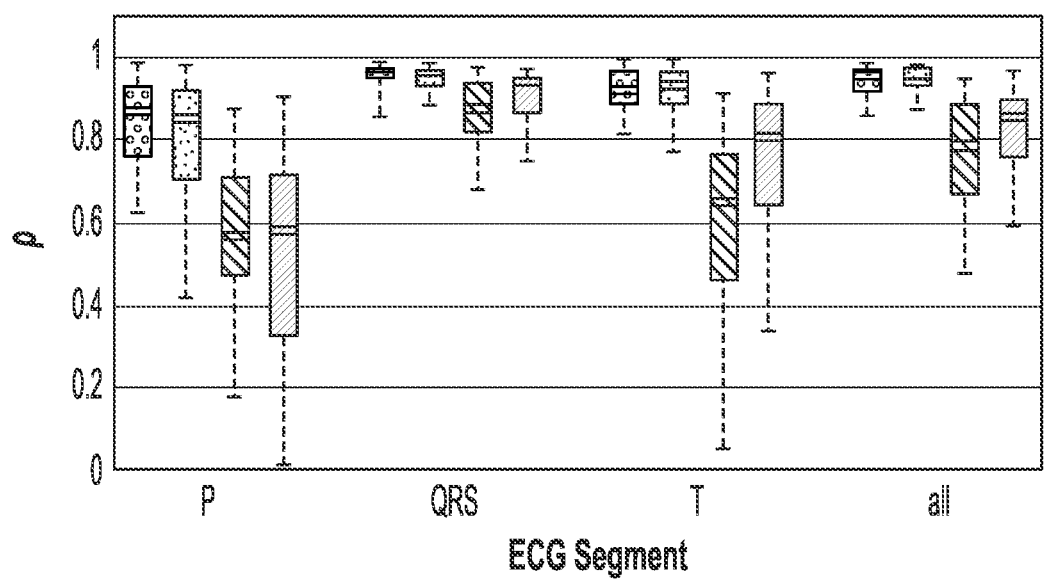
FIG. 10(b) illustrates another comparison of the performance of a method in a test set of the MIMIC-III database in different combinations of the disease types and test modes, according to certain embodiments.

FIG. 10(a) illustrates a comparison of the performance of a method in test set of the MIMIC-III database in different combinations of the disease types and test modes, according to certain embodiments. Further, FIG. 10(b) illustrates another comparison of the performance of a method in test set of the MIMIC-III database in different combinations of the disease types and test modes, according to certain embodiments. For instance, statistics of the (a) rRMSE and (b) ρ are summarized using the box plots.

The statistics reveal that overall non-cardiac cases give better performance than cardiac cases as less variation exists in the morphology of non-cardiac ECG signals. The model trained in the SD mode gives better performance compared with that trained in the SI mode in this dataset, which suggests that H in (2) and b(t) in (3) may be subject dependent. In general, for the SD mode, the average performance in ρ on T wave is about 0.90 and on QRS wave is about 0.94 using R2R, much higher than those on the P wave, which is in accordance with the first experiment.

Figure 11A:
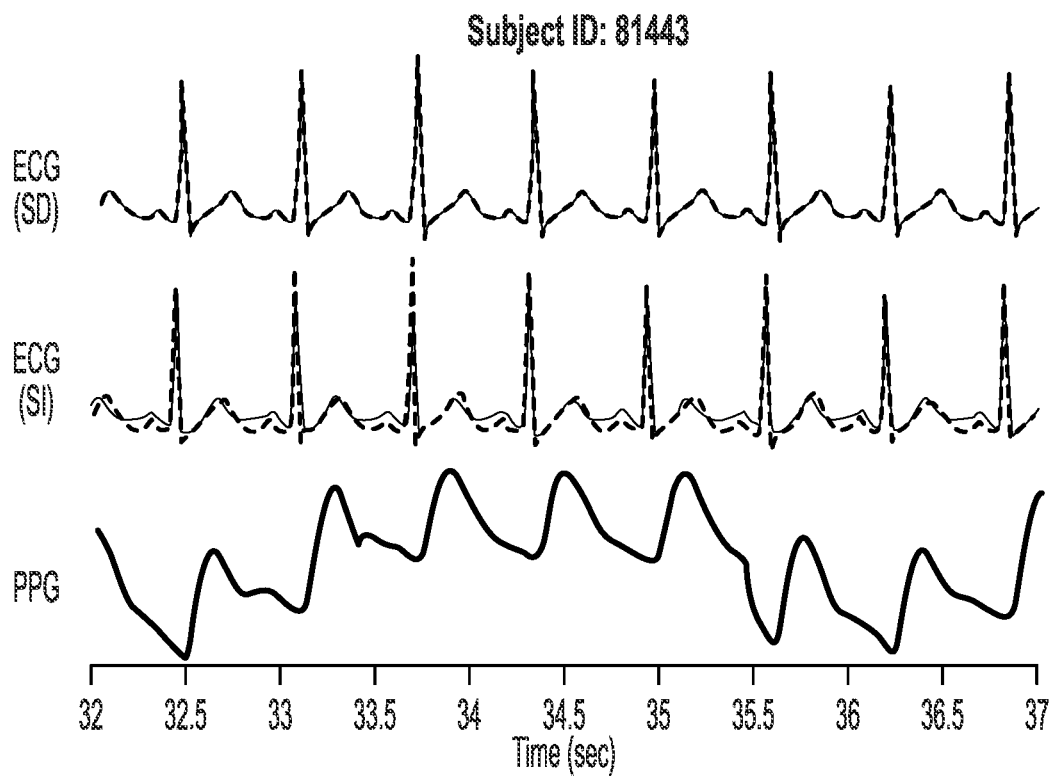
FIG. 11(a) illustrates a quantitative comparison between the reconstructed ECG signals tested in the SD (1st row) and SI (2nd row) mode from the MIMIC-III database, according to certain embodiments.
Figure 11B:
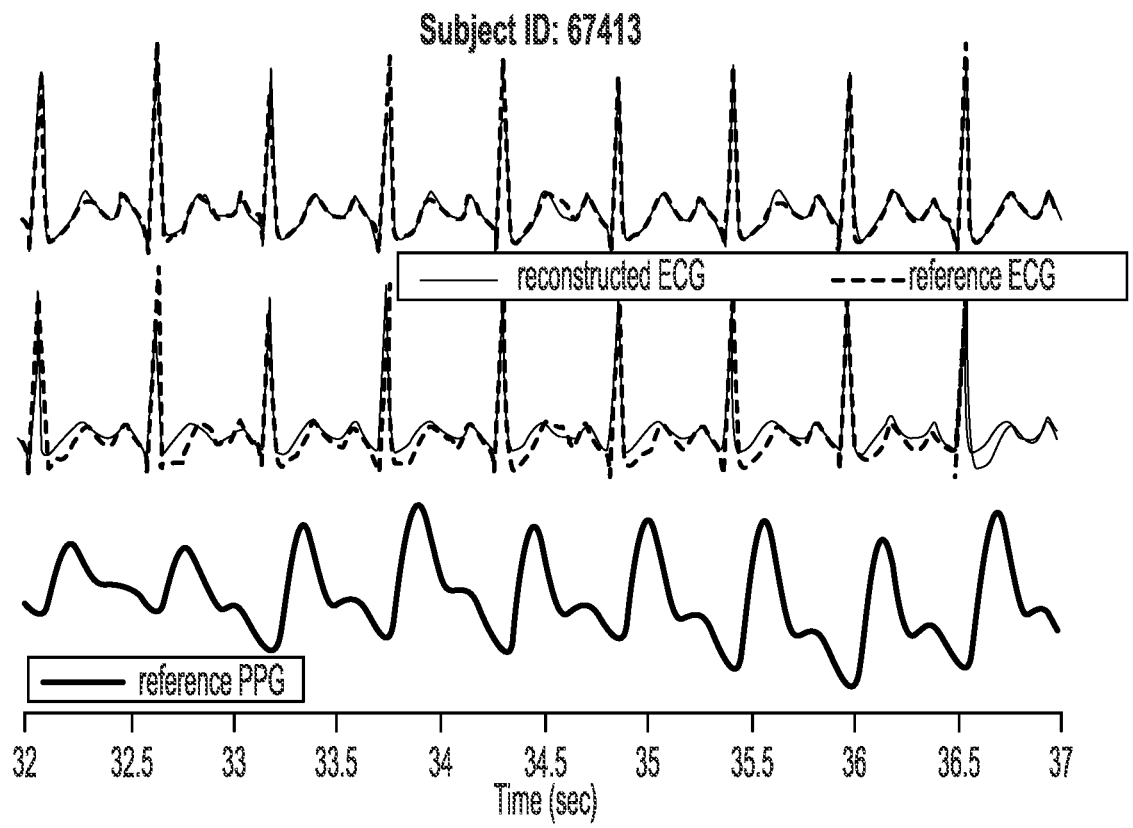
FIG. 11(b) illustrates another quantitative comparison between the reconstructed ECG signals tested in the SD (1st row) and SI (2nd row) mode from the MIMIC-III database, according to certain embodiments.

FIGS. 11(a) and 11(b) illustrate two qualitative comparisons between the reconstructed ECG signals tested in the SD (1st row) and SI (2nd row) mode from the MIMIC-III database, according to certain embodiments. Specifically, FIG. 11(a) illustrates signals of a 54-year-old male subject with upper gastrointestinal bleeding. The Pearson's correlation coefficients in this case are 0.969 in the SD mode, and 0.923 in the SI mode. FIG. 11(b) illustrates a 52-year-old male subject with congestive heart failure. Here, the correlation coefficients are 0.959 in the SD mode, and 0.881 in the SI mode. Further, in FIGS. 11(a) and 11(b), two five-second segments of the reconstructed ECG waveform are shown in the test set from the two subjects using the R2R cycle segmentation scheme with $L_x=18$ in the SI mode and $L_x=12$ in the SD mode. It can be seen from both plots that the system retains the major shape of the original ECG waveform except for the P waves of the first subject and S waves of the second subject in the SI mode. In addition, the system almost perfectly reconstructs the shape of the ECG waveform in the SD mode.

In addition to quantitative analysis of the reconstruction performance by Pearson correlation and rRMSE, a disease classification experiment was also executed on the reconstructed ECG signals to show the potential of the method in applications within biomedical health informatics.

First, from the collected MIMIC-III database 28 patients with five types of cardiac diseases were selected, including congestive heart failure, ST-segment elevated myocardial infarction, non-ST segment elevated myocardial infarction, hypotension, and coronary artery disease. For each patient, the SD mode ECG reconstruction experiment was performed to obtain the reconstructed ECG signals. To simulate the diagnosis process of cardiologists, the cycle-wise ECG signals were connected into pieces of 30-cycle length for training and classification. The training data was composed of 70% from the original ECG signals, and the testing data constitutes of the rest 30% from original ECG signals and all of the reconstructed ECG signals.

FIGS. 12(a)-12(c) illustrate confusion matrices for classification results using kernel SVM on three types of data. In particular, FIG. 12(a) illustrates a confusion matrix for classification on the original ECG, FIG. 12(b) illustrates a confusion matrix for classification on the inferred ECG, and FIG. 12(c) illustrates a confusion matrix on the original PG. PCA was applied for dimensionality reduction and support vector machine (SVM) classifier with polynomial kernel from the SVM library (e.g., an online library for support vector machines). The confusion matrices for classification are illustrated in FIGS. 12(a)-12(c) with the reduced dimension equaling 100. Comparing FIGS. 12(a) and 12(b), it can be concluded that the reconstructed ECG has a comparable classification performance as the original ECG signals. The confusion matrix was also included for original PPG classification in FIG. 12(c) for reference. The superior performance of classification from the reconstructed ECG signals compared to that of the original PPG signal indicates the fidelity of the reconstructed ECG recordings in the presence of cardiac pathologies.

Experiment 3: Human Subject Data

The temporal consistency of the system was tested with the data using consumer-grade sensors. Two subjects participated in this two-weeks long experiment. According to the most-recent medical examinations received by both subjects, none of them had been diagnosed with any known CVDs or mental illness. Six 5-min sessions were recorded for the first subject and seven sessions for the second subject in different times over a two-week period. In each session, the subjects were asked to wear two devices, namely, EMAY FDA-clear handheld single-lead ECG monitor (Model: EMG-10), and CONTEC pulse oximeter (Model: CMS50E) to record their lead I bipolar ECG signals and finger-tip PPG signals simultaneously. The subjects were asked to wear the PPG sensor on his/her index finger of the right hand, and attach the electrodes of the ECG sensor to the palm of the left hand and the back of the right hand. The subjects were asked to sit in front of a table and put their arms on the table as motionless and peacefully as possible to reduce the motion-induced artifacts during the recording time. The sampling rates of the ECG and PPG sensors were 150 and 60 Hz, respectively. In addition, Both signals were up-sampled to 300 Hz via the bilinear interpolation for consistency consideration, and the pair of signals were properly aligned.

The system performance was evaluated in three training modes. The first mode includes a session dependent (SessD) mode, which is the same as the SD mode. Here, F* was trained and tested separately in each session. The second mode includes a session independent (SessI) mode, where the sessions of each subject were first listed chronologically. F* was trained on the first 80% of the sessions, and was tested on the rest of the sessions in order to maximize the temporal difference of the training and test set. The third mode includes a subject independent (SubjI) mode where the subject dependent raining sets were combined and used in SessI mode, and trained a subject independent model to test on the same test set in SessI mode.

Figure 13:
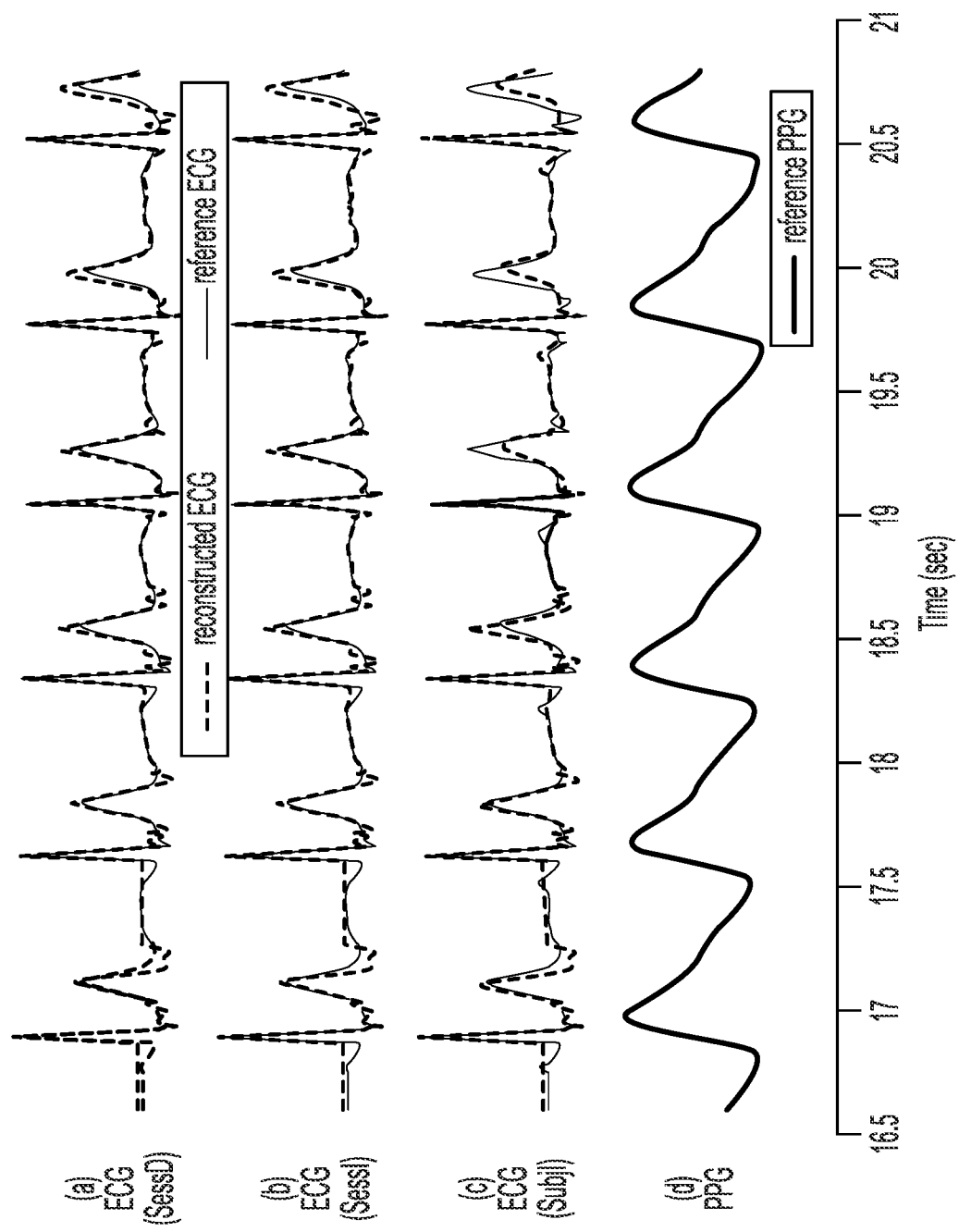
FIG. 13 illustrates one example of the reconstructed waveforms from the 6th session of the first subject, according to certain embodiments.

In this experiment, the R2R segmentation scheme was used, and $L_x=12$ in SessD and SessI mode and $L_x=18$ in SubjI mode were set. The cycle segmentation process was guided by peak detection algorithms. The PPG peak detection algorithm is based on the analysis of the first derivative of the PPG waveform. Further, the ECG peak detection algorithm is based on the length transformation of the ECG waveform, using a nonlinearly-scaled ECG curve length feature. The two algorithms were deployed to detect the R peak of ECG and the onset point of the PPG signal, respectively. FIG. 13 illustrates one example of the reconstructed waveforms from the 6th session of the first subject, according to certain embodiments. It is noted that this session was recorded more than one week after the other sessions. From the qualitative result in 2nd and 3rd rows of FIG. 13, it can be seen that the reconstructed signals match well with the reference ECG in all waves in the condition of long temporal separation from the training set.

The average performance in different combinations of training modes and regression methods were summarized, and each combination in terms of rRMSE and ρ in P, QRS, T waves respectively, were evaluated. In general, it was noticed that the system performed best in SessD mode, followed by SessI and SubjI. This difference may suggest possible subject-wise difference of the model parameter b(t), H, or α. Consistent observations in this dataset also included better performance in T wave than P wave.

Cycle Segmentation via PPG

The system in the above-described experiments were evaluated assuming the availability of the ground truth cardiac cycle information obtained from the ECG signal. A more practical setting may also be evaluated when the cycles are estimated solely from the PPG signal, thereby accounting for the real-world constraint that the reference cycle information is unavailable.

In certain embodiments, MIMIC-III database introduced above was adopted in this experiment. The PPG and ECG signal pair was segmented according to the onset points of the PPG signal, considering the onset point represents one of the most distinct features within the PPG cycle. This segmentation scheme may be identified as an onset-to-onset (O2O) segmentation scheme based on the onset of the PPG signal.

To single out the contribution to the reconstruction error due to the discrepancy in the waveform shape rather than the misalignment of the ECG peaks, O2O was evaluated after each reconstructed cycle was post-processed to align with the original ECG signal. This was done by shifting each reconstructed ECG cycle in time so that the original and reconstructed ECG signals were matched according to their R peaks. The performance statistics reveal that the shape of the waveform is inferred well, and increased error in reconstruction by O2O compared with R2R is mainly due to the misalignment of the signal that has a sample mean and standard deviation of 0.38% and 3.98% in relative cycle length, respectively. This observation was consistent across the SI and SD training modes.

The disease classification experiment was conducted using the O2O segmentation without the peak alignment. A comparable classification accuracy of the reconstructed ECG signal was observed compared with the result when the model was trained with the R2R segmentation. This observation indicated that the ECG reconstruction deviation did not affect the diagnostic power of the reconstructed ECG signal.

Extensions of the Methodology

Figure 14:
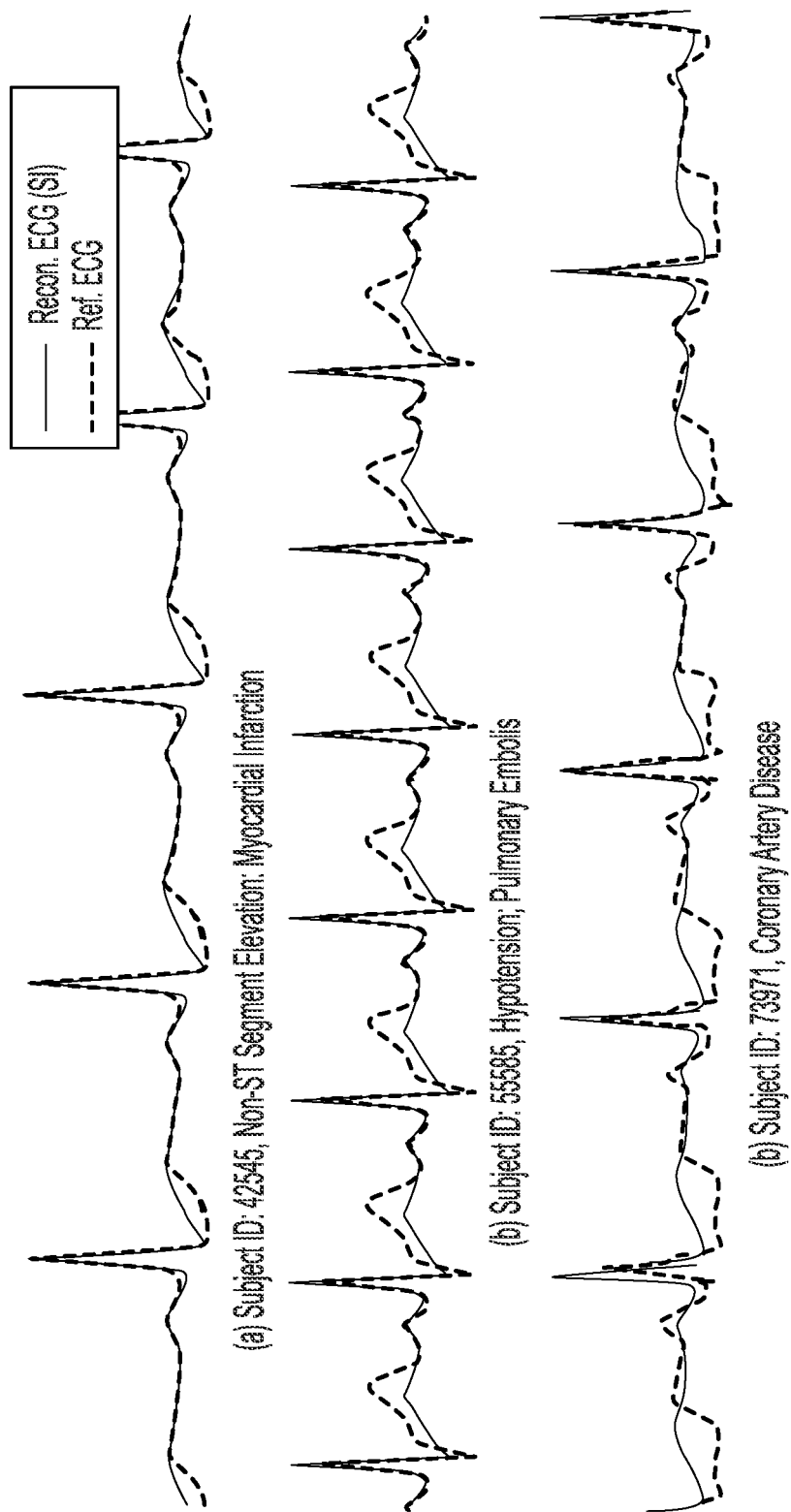
FIG. 14 illustrates three examples of 5-second long reconstructed ECG signals from the MIMIC-III database using a subject independent model in MIMIC-III database that do not fully capture some detailed characteristics of the original ECG signal, according to certain embodiments.

Certain embodiments may provide improvements to the system for situations where some subjects with cardiac complications influence the morphology of ECG waves. In such cases, the model and the corresponding methodology using DCT representations may have an affect on the ECG signals from PPG, such as, for example, when the model is trained in the SI mode. For instance, FIG. 14 illustrates three examples of 5-second long reconstructed ECG signals from the MIMIC-III database using a subject independent model in MIMIC-III database that do not capture certain characteristics of the original ECG signal, according to certain embodiments. In particular, FIG. 14 illustrates three examples of the reconstructed ECG signals of low performance in the presence of different pathologies of the ECG signal. The reconstructed ECGs do not capture certain aspects of the waveform during the elevation of the T wave (a, b, c), the T wave (b, c), and the P wave (c). Some other cases that may influence the system performance may include motion-induced artifacts and loose contact artifacts in PPG recordings under ambulatory conditions. However, certain embodiments can remedy these effects by providing a more sophisticated training system and a larger database.

Certain embodiments may provide more model flexibility in reconstruction, the mapping F is not limited to a linear transform, but can be generalized to nonlinear mappings or transforms (for example, neural networks) and harness more patient data and medical knowledge. Also, the analysis channel of the system may not be limited to DCT, but can be of other analytical forms, including discrete wavelet transform, discrete Fourier transform, or other mapping jointly learned with F. According to certain embodiments, with further exploration of datasets with detailed profiles of subjects and larger size of data, a more complex model or a more general model can be learned based on biomedical, statistical, and physical meanings of the signals to capture the relation of PPG and ECG better. In addition, since ECG is a more adequate and important indicator than PPG for many cardiovascular diseases (CVDs), it has the potential that the developed model, along with the reconstructed ECG, has a significant implication on CVD inference.

Figure 15:
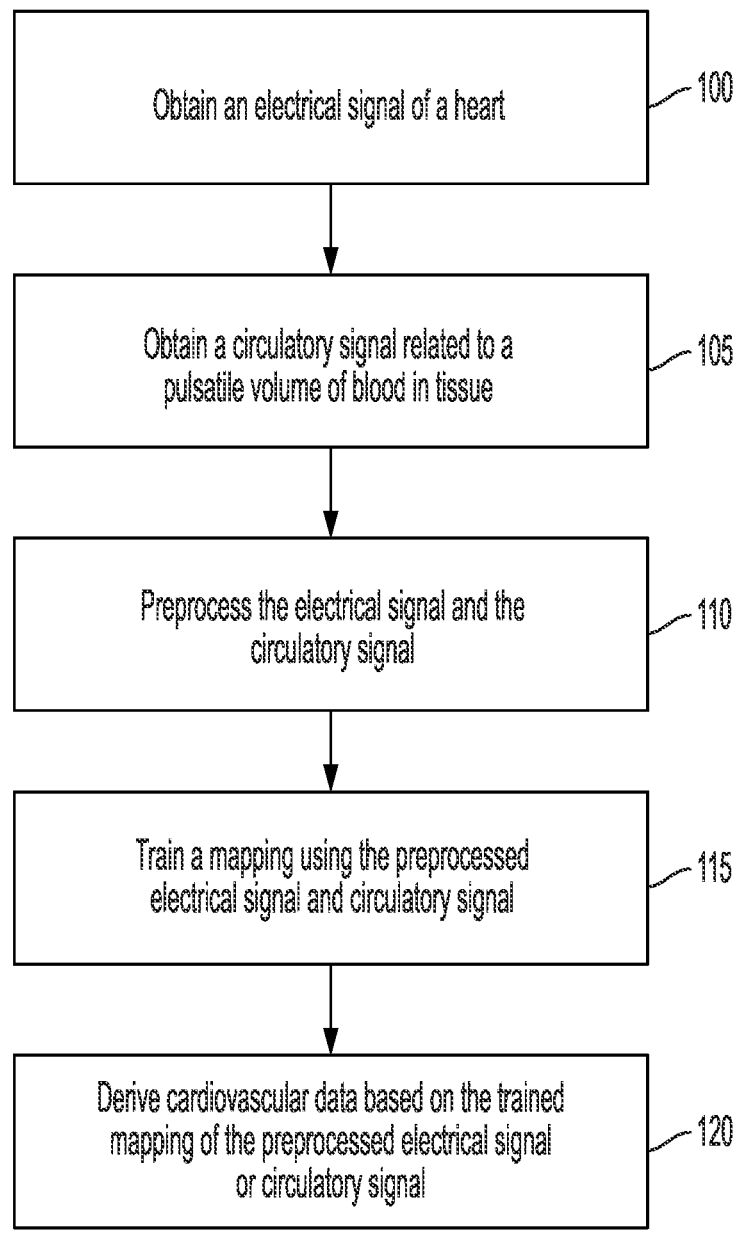
FIG. 15 illustrates a flow diagram of a method, according to certain embodiments.

FIG. 15 illustrates an example flow diagram of a method, according to an example embodiment. In certain example embodiments, the flow diagram of FIG. 15 may be performed by a system that includes an ECG apparatus, a PPG apparatus, and a computer apparatus. According to certain embodiments, each of these apparatuses of the system may be represented by, for example, an apparatus similar to apparatus 10 illustrated in FIG. 16. According to one example embodiment, the method of FIG. 15 may include, at 100, obtaining an electrical signal of a heart. The method may also include, at 105, obtaining a circulatory signal related to a pulsatile volume of blood in tissue. The method may further include, at 110, preprocessing the electrical signal and the circulatory signal. In addition, the method may include, at 115, training a mapping using the preprocessed electrical signal and circulatory signal. Further, the method may include, at 120, deriving cardiovascular data based on the trained mapping of the preprocessed electrical signal or circulatory signal.

In certain embodiments, deriving cardiovascular data may include reconstructing the electrical signal for the same or different heart based on the trained mapping of the circulatory signal. In another embodiment, the preprocessing may include performing a two-level signal alignment scheme of the electrical signal and the circulatory signal. In another embodiment, the two-level signal alignment scheme may include estimating a cycle-wise delay using peak features of the electrical signal and the circulatory signal, and aligning the electrical signal with the circulatory signal based on a physical meaning and correspondence of the electrical signal and the circulatory signal. According to certain embodiments, the preprocessing may also include estimating trends from the electrical signal and the circulatory signal, and subtracting the trends from an original electrical signal and an original circulatory signal. According to another embodiment, the preprocessing may include segmenting each cycle of the electrical signal and each cycle of the circulatory signal. In certain embodiments, the segmenting may include an SR segmenting scheme and an R peak-to-R peak segmenting scheme.

In a further embodiment, the preprocessing may include scaling each cycle sample in time and amplitude to make it of equal length, zero mean, and unit sample standard deviation. According to another embodiment, the training may include learning a linear transform, which maps from the circulatory signal to discrete cosine transform coefficients of the electrical signal. According to a further embodiment, the training may include learning a non-linear transform, which maps a component of the circulatory signal to a component of the electrical signal. In certain embodiments, the reconstructing may include applying an inverse discrete cosine transform to the trained mapping of the discrete cosine transform coefficients of the circulatory signal.

Figure 16:
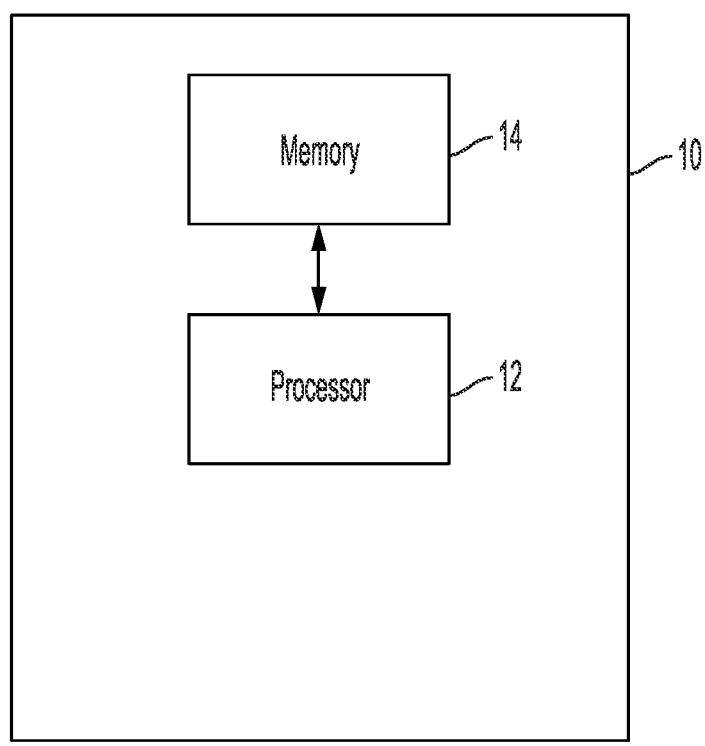
FIG. 16 illustrates an apparatus, according to certain embodiments.

FIG. 16 illustrates an apparatus 10 according to an example embodiment. Although only one apparatus is illustrated in FIG. 16, the apparatus may represent multiple apparatus as part of a system or network. For example, in certain embodiments, apparatus 10 may be an ECG apparatus, PPG apparatus, or computer apparatus that operate individually or together as a system.

In some embodiments, the functionality of any of the methods, processes, algorithms or flow charts described herein may be implemented by software and/or computer program code or portions of code stored in memory or other computer readable or tangible media, and executed by a processor.

For example, in some embodiments, apparatus 10 may include one or more processors, one or more computer-readable storage medium (for example, memory, storage, or the like), one or more radio access components (for example, a modem, a transceiver, or the like), and/or a user interface. It should be noted that one of ordinary skill in the art would understand that apparatus 10 may include components or features not shown in FIG. 16.

As illustrated in the example of FIG. 16, apparatus 10 may include or be coupled to a processor 12 for processing information and executing instructions or operations. Processor 12 may be any type of general or specific purpose processor. In fact, processor 12 may include one or more of general-purpose computers, special purpose computers, microprocessors, digital signal processors (DSPs), field-programmable gate arrays (FPGAs), application-specific integrated circuits (ASICs), and processors based on a multi-core processor architecture, as examples. While a single processor 12 is shown in FIG. 16, multiple processors may be utilized according to other embodiments. For example, it should be understood that, in certain example embodiments, apparatus 10 may include two or more processors that may form a multiprocessor system (e.g., in this case processor 12 may represent a multiprocessor) that may support multiprocessing. According to certain example embodiments, the multiprocessor system may be tightly coupled or loosely coupled (e.g., to form a computer cluster).

Processor 12 may perform functions associated with the operation of apparatus 10 including, as some examples, precoding of antenna gain/phase parameters, encoding and decoding of individual bits forming a communication message, formatting of information, and overall control of the apparatus 10, including processes illustrated in FIGS. 1-15.

Apparatus 10 may further include or be coupled to a memory 14 (internal or external), which may be coupled to processor 12, for storing information and instructions that may be executed by processor 12. Memory 14 may be one or more memories and of any type suitable to the local application environment, and may be implemented using any suitable volatile or nonvolatile data storage technology such as a semiconductor-based memory device, a magnetic memory device and system, an optical memory device and system, fixed memory, and/or removable memory. For example, memory 14 can be comprised of any combination of random access memory (RAM), read only memory (ROM), static storage such as a magnetic or optical disk, hard disk drive (HDD), or any other type of non-transitory machine or computer readable media. The instructions stored in memory 14 may include program instructions or computer program code that, when executed by processor 12, enable the apparatus 10 to perform tasks as described herein.

In certain embodiments, apparatus 10 may further include or be coupled to (internal or external) a drive or port that is configured to accept and read an external computer readable storage medium, such as an optical disc, USB drive, flash drive, or any other storage medium. For example, the external computer readable storage medium may store a computer program or software for execution by processor 12 and/or apparatus 10 to perform any of the methods illustrated in FIGS. 1-15.

Additionally or alternatively, in some embodiments, apparatus 10 may include an input and/or output device (I/O device). In certain embodiments, apparatus 10 may further include a user interface, such as a graphical user interface or touchscreen.

In certain embodiments, memory 14 stores software modules that provide functionality when executed by processor 12. The modules may include, for example, an operating system that provides operating system functionality for apparatus 10. The memory may also store one or more functional modules, such as an application or program, to provide additional functionality for apparatus 10. The components of apparatus 10 may be implemented in hardware, or as any suitable combination of hardware and software. According to certain example embodiments, processor 12 and memory 14 may be included in or may form a part of processing circuitry or control circuitry.

As used herein, the term "circuitry" may refer to hardware-only circuitry implementations (e.g., analog and/or digital circuitry), combinations of hardware circuits and software, combinations of analog and/or digital hardware circuits with software/firmware, any portions of hardware processor(s) with software (including digital signal processors) that work together to cause an apparatus (e.g., apparatus 10) to perform various functions, and/or hardware circuit(s) and/or processor(s), or portions thereof, that use software for operation but where the software may not be present when it is not needed for operation. As a further example, as used herein, the term "circuitry" may also cover an implementation of merely a hardware circuit or processor (or multiple processors), or portion of a hardware circuit or processor, and its accompanying software and/or firmware.

According to certain embodiments, apparatus 10 may be controlled by memory 14 and processor 12 to perform functions associated with example embodiments described herein. For instance, in certain embodiments, apparatus 10 may be controlled by memory 14 and processor 12 to obtain an electrical signal of a heart. Apparatus 10 may also be controlled by memory 14 and processor 12 to obtain a circulatory signal related to a pulsatile volume of blood in tissue. Apparatus 10 may further be controlled by memory 14 and processor 12 to preprocess the electrical signal and the circulatory signal. Further, apparatus 10 may be controlled by memory 14 and processor 12 to train a mapping using the preprocessed electrical signal and circulatory signal. In addition, apparatus 10 may be controlled by memory 14 and processor 12 to derive cardiovascular data based on the trained mapping of the preprocessed electrical signal or circulatory signal.

Further embodiments may provide means for performing any of the functions, steps, or procedures described herein. For example, certain embodiments may be directed to an apparatus that includes means for obtaining an electrical signal of a heart. The apparatus may also include means for obtaining a circulatory signal related to a pulsatile volume of blood in tissue. In addition, the apparatus may include means for preprocessing the electrical signal and the circulatory signal. The apparatus may further include means for training a mapping using the preprocessed electrical signal and circulatory signal. Further, the apparatus may include means for deriving cardiovascular data based on the trained mapping of the preprocessed electrical signal or circulatory signal.

Certain example embodiments described herein provide several technical improvements, enhancements, and /or advantages. In some example embodiments, it may be possible to show in various datasets that the system can reconstruct ECG signals from PPG measurements with high accuracy by exploiting the relation of these two types of cardiovascular related measurements. For instance, certain embodiments can achieve a high prediction accuracy greater than 0.92 in average correlation for each dataset when the model is trained subject-wise. According to other embodiments, it may be possible to provide a signal processing and learning system that is designed synergistically, providing the ability to reconstruct ECG signals by exploiting the relation of ECG and PPG cardiovascular measurements.

Certain embodiments may also open up a new direction for cardiac medical practitioners, wearable technologists, and data scientists to leverage a rich body of clinical ECG knowledge and transfer the understanding to build a knowledge base from PPG and other data from wearable devices. In addition, other embodiments may provide a more user-friendly, low-cost, continuous, and long-term cardiac monitoring that supports and promotes public health, especially for people with special needs. Such reconstruction can also take advantage of both the rich clinical knowledge base of ECG signal and the easy accessibility of the PPG signal.

A computer program product may comprise one or more computer-executable components which, when the program is run, are configured to carry out some example embodiments. The one or more computer-executable components may be at least one software code or portions of it. Modifications and configurations required for implementing functionality of an example embodiment may be performed as routine(s), which may be implemented as added or updated software routine(s). Software routine(s) may be downloaded into the apparatus.

As an example, software or a computer program code or portions of it may be in a source code form, object code form, or in some intermediate form, and it may be stored in some sort of carrier, distribution medium, or computer readable medium, which may be any entity or device capable of carrying the program. Such carriers may include a record medium, computer memory, read-only memory, photoelectrical and/or electrical carrier signal, telecommunications signal, and software distribution package, for example. Depending on the processing power needed, the computer program may be executed in a single electronic digital computer or it may be distributed amongst a number of computers. The computer readable medium or computer readable storage medium may be a non-transitory medium.

In other example embodiments, the functionality may be performed by hardware or circuitry included in an apparatus (e.g., apparatus 10), for example through the use of an application specific integrated circuit (ASIC), a programmable gate array (PGA), a field programmable gate array (FPGA), or any other combination of hardware and software. In yet another example embodiment, the functionality may be implemented as a signal, a non-tangible means that can be carried by an electromagnetic signal downloaded from the Internet or other network.

According to an example embodiment, an apparatus, such as a device, or a corresponding component, may be configured as circuitry, a computer or a microprocessor, such as single-chip computer element, or as a chipset, including at least a memory for providing storage capacity used for arithmetic operation and an operation processor for executing the arithmetic operation.

One having ordinary skill in the art will readily understand that the invention as discussed above may be practiced with steps in a different order, and/or with hardware elements in configurations which are different than those which are disclosed. Therefore, although the invention has been described based upon these example embodiments, it would be apparent to those of skill in the art that certain modifications, variations, and alternative constructions would be apparent, while remaining within the spirit and scope of example embodiments.

PARTIAL GLOSSARY

AV Atrioventricular
CVD Cardiovascular Disease
DCT Discrete Cosine Transform
ECG Electrocardiogram
HRV Heart Rate Variability
PPG Photoplethysmogram
SA Sinoatrial
SD Subject Dependent
SI Subject Independent

We claim:

1. A method for cardiovascular monitoring and analytics, comprising:
   obtaining an electrical signal of a heart;
   obtaining a circulatory signal related to a pulsatile volume of blood in tissue;
   preprocessing the electrical signal and the circulatory signal by estimating trends from the electrical signal and the circulatory signal, and subtracting the trends from an original electrical signal and an original circulatory signal;
   training a mapping using the preprocessed electrical signal and circulatory signal; and
   deriving cardiovascular data based on the trained mapping of the preprocessed electrical signal or circulatory signal.

2. The method for cardiovascular monitoring and analytics according to claim 1, wherein deriving cardiovascular data comprises reconstructing the electrical signal for the same or different heart based on the trained mapping of the circulatory signal.

3. The method for cardiovascular monitoring and analytics according claim 2, wherein the reconstructing comprises applying an inverse discrete cosine transform to the trained mapping of discrete cosine transform coefficients of the circulatory signal.

4. The method for cardiovascular monitoring and analytics according to claim 1, wherein the preprocessing comprises performing a two-level signal alignment scheme of the electrical signal and the circulatory signal.

5. The method for cardiovascular monitoring and analytics according to claim 4, wherein the two-level signal alignment scheme comprises:
   estimating a cycle-wise delay using peak features of the electrical signal and the circulatory signal; and
   aligning the electrical signal with the circulatory signal based on a physical meaning and correspondence of the electrical signal and the circulatory signal.

6. The method for cardiovascular monitoring and analytics according to claim 1, wherein the preprocessing comprises segmenting each cycle of the electrical signal and each cycle of the circulatory signal.

7. The method for cardiovascular monitoring and analytics according to claim 6, wherein the segmenting comprises an SR segmenting scheme and an R peak-to-R peak segmenting scheme.

8. The method for cardiovascular monitoring and analytics according to claim 1, wherein the preprocessing comprises scaling each cycle sample in time and amplitude to make it of equal length, zero mean, and unit sample standard deviation.

9. The method for cardiovascular monitoring and analytics according to claim 1, wherein the training comprises learning a linear transform, which maps from discrete cosine transform coefficients of the circulatory signal to discrete cosine transform coefficients of the electrical signal.

10. The method for cardiovascular monitoring and analytics according to claim 1, wherein the training comprises learning a non-linear transform, which maps a component of the circulatory signal to a component of the electrical signal.

11. An apparatus, comprising:
    at least one processor; and
    at least one memory comprising computer program code, the at least one memory and the computer program code are configured, with the at least one processor to cause the apparatus at least to
    obtain an electrical signal of a heart,
    obtain a circulatory signal related to a pulsatile volume of blood in tissue,
    preprocess the electrical signal and the circulatory signal by estimating trends from the electrical signal and the circulatory signal, and subtracting the trends from an original electrical signal and an original circulatory signal,
    train a mapping using the preprocessed electrical signal and circulatory signal, and
    derive cardiovascular data based on the trained mapping of the preprocessed electrical signal or circulatory signal.

12. The apparatus according to claim 11, wherein deriving cardiovascular data comprises reconstructing the electrical signal for the same or different heart based on the trained mapping of the circulatory signal.

13. The apparatus according to claim 11, wherein the preprocessing comprises performing a two-level signal alignment scheme of the electrical signal and the circulatory signal.

14. The apparatus according to claim 11, wherein the two-level signal alignment scheme comprises:
    estimating a cycle-wise delay using peak features of the electrical signal and the circulatory signal; and
    aligning the electrical signal with the circulatory signal based on a physical meaning and correspondence of the electrical signal and the circulatory signal.

15. The apparatus according to claim 11, wherein the preprocessing comprises segmenting each cycle of the electrical signal and each cycle of the circulatory signal.

16. The apparatus according to claim 15, wherein the segmenting comprises an SR segmenting scheme and an R peak-to-R peak segmenting scheme.

17. The apparatus according to claim 11, wherein the preprocessing comprises scaling each cycle sample in time and amplitude to make it of equal length, zero mean, and unit sample standard deviation.

18. A computer program embodied on a non-transitory computer readable medium, the computer program, when executed by a processor, causes the processor to:
    obtain an electrical signal of a heart;
    obtain a circulatory signal related to a pulsatile volume of blood in tissue;
    preprocess the electrical signal and the circulatory signal by estimating trends from the electrical signal and the circulatory signal, and subtracting the trends from an original electrical signal and an original circulatory signal;
    train a mapping using the preprocessed electrical signal and circulatory signal; and
    derive cardiovascular data based on the trained mapping of the preprocessed electrical signal or circulatory signal.

* * * * *